United States Patent
Ben-Yedidia et al.

(10) Patent No.: US 9,303,070 B2
(45) Date of Patent: Apr. 5, 2016

(54) MULTIMERIC MULTIEPITOPE POLYPEPTIDES IN IMPROVED SEASONAL AND PANDEMIC INFLUENZA VACCINES

(75) Inventors: Tamar Ben-Yedidia, Mazkeret Batya (IL); George H. Lowell, Jerusalem (IL)

(73) Assignee: BiondVax Pharmaceuticals Ltd., Ness Ziona (IL)

( * ) Notice: Subject to any disclaimer, the term of this patent is extended or adjusted under 35 U.S.C. 154(b) by 80 days.

(21) Appl. No.: 14/000,815

(22) PCT Filed: Feb. 22, 2011

(86) PCT No.: PCT/IL2011/000178
§ 371 (c)(1),
(2), (4) Date: Dec. 26, 2013

(87) PCT Pub. No.: WO2012/114323
PCT Pub. Date: Aug. 30, 2012

(65) Prior Publication Data
US 2014/0227306 A1 Aug. 14, 2014

(51) Int. Cl.
*C07K 14/005* (2006.01)
*A61K 39/145* (2006.01)
*A61K 39/12* (2006.01)
*A61K 39/00* (2006.01)

(52) U.S. Cl.
CPC .............. *C07K 14/005* (2013.01); *A61K 39/12* (2013.01); *A61K 39/145* (2013.01); *A61K 2039/545* (2013.01); *A61K 2039/55* (2013.01); *A61K 2039/55566* (2013.01); *A61K 2039/58* (2013.01); *A61K 2039/645* (2013.01); *A61K 2039/70* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| 4,436,727 A | 3/1984 | Ribi |
|---|---|---|
| 4,474,757 A | 10/1984 | Arnon et al. |
| 4,539,205 A | 9/1985 | Goodman |
| 4,643,992 A | 2/1987 | Goodman |
| 4,767,842 A | 8/1988 | Stevens |
| 4,866,034 A | 9/1989 | Ribi |
| 4,987,237 A | 1/1991 | Myers et al. |
| 5,011,828 A | 4/1991 | Goodman |
| 5,057,540 A | 10/1991 | Kensil |
| 5,093,318 A | 3/1992 | Goodman |
| 5,683,695 A | 11/1997 | Shen et al. |
| 5,709,879 A | 1/1998 | Barchfeld |
| 5,750,110 A | 5/1998 | Prieels et al. |
| 5,776,468 A | 7/1998 | Hauser et al. |
| 5,977,081 A | 11/1999 | Marciani |
| 6,022,960 A | 2/2000 | Potter et al. |
| 6,063,386 A | 5/2000 | Dale et al. |
| 6,080,725 A | 6/2000 | Marciani |
| 6,086,901 A | 7/2000 | O'Hagan |
| 6,113,918 A | 9/2000 | Johnson |
| 6,130,082 A | 10/2000 | Majarian et al. |
| 6,303,347 B1 | 10/2001 | Johnson |
| 6,355,257 B1 | 3/2002 | Johnson |
| 6,740,325 B1 | 5/2004 | Arnon |
| 6,828,416 B1 | 12/2004 | Lal et al. |
| 6,843,781 B2 | 1/2005 | Alchas |
| 7,063,967 B2 | 6/2006 | Johnson et al. |
| 7,147,862 B1 | 12/2006 | Prieels et al. |
| 7,250,036 B2 | 7/2007 | Alchas |
| 7,260,958 B2 | 8/2007 | Huang |
| 7,323,182 B2 | 1/2008 | Garcon |
| 7,794,731 B2 | 9/2010 | Mizel et al. |
| 2003/0092643 A1 | 5/2003 | Johnson |
| 2004/0077540 A1 | 4/2004 | Quay |
| 2004/0223976 A1 | 11/2004 | Bianchi et al. |
| 2009/0104216 A1 | 4/2009 | Torres |
| 2009/0304730 A1 | 12/2009 | Arnon et al. |
| 2010/0047275 A1 | 2/2010 | Stoloff et al. |
| 2010/0158943 A1 | 6/2010 | Vajdy et al. |
| 2010/0189741 A1* | 7/2010 | Ballou et al. ............... 424/202.1 |

FOREIGN PATENT DOCUMENTS

| EP | 0399843 | 11/1990 |
|---|---|---|
| EP | 0671948 | 8/1997 |
| EP | 0689454 | 9/1997 |
| WO | WO93/14206 A2 | 7/1993 |
| WO | WO93/20846 A1 | 10/1993 |
| WO | 95/17210 | 6/1995 |
| WO | 96/02555 | 2/1996 |
| WO | 96/33739 | 10/1996 |
| WO | 97/30721 | 8/1997 |
| WO | WO99/07839 A2 | 2/1999 |
| WO | WO99/12565 A1 | 3/1999 |

(Continued)

OTHER PUBLICATIONS

Ada and Jones (1986) The immune response to influenza infection. Curr Top Microbial Immunol 128:1-54 Adar et al., (2009) A universal epitope-based influenza vaccine and its efficacy against H5N1. Vaccine 27(15): 2099-2107.
Arnon et al., (2001) Peptide-based synthetic recombinant vaccines with anti-viral efficacy. Biologicals 29(3-4):237-242.
Baker (1988) Inactivation of suppressor T-cell activity by nontoxic monophosphoryl lipid A. Infect Immun 56(5):1076-1083.
Ben-Yedidia and Arnon (2005) Review: Towards an epitope-based human vaccine for influenza. Hum Vaccin 1(3): 95-101.
Ben-Yedidia et al., (1999) Intranasal administration of peptide vaccine protects human/mouse radiation chimera from influenza infection, Int Immunol 11(7):1043-1051.
Ben-Yedidia et al., XP000914823, (1998) Efficacy of anti-influenza peptide vaccine in aged mice. Mech Ageing Dev 104(1)11-23.
Caro-Aguilar et al., (2005) Chimeric epitopes delivered by polymeric synthetic linear peptides induce protective immunity to malaria. Microbes Infect 7(13): 1324-1337.

(Continued)

*Primary Examiner* — Agnieszka Boesen
(74) *Attorney, Agent, or Firm* — Winston & Strawn LLP

(57) ABSTRACT

The present invention relates to use of multimeric multi-epitope peptide-based compositions for immunizing subjects against influenza by administering the compositions to the subject prior to or together with seasonal or pandemic influenza vaccines. The present invention also relates to compositions that include a multimeric multi-epitope polypeptide and a seasonal or pandemic preparation against influenza.

9 Claims, 9 Drawing Sheets

(56) References Cited

FOREIGN PATENT DOCUMENTS

| WO | 99/52549 | 10/1999 |
|---|---|---|
| WO | 99/56776 | 11/1999 |
| WO | WO00/32228 A2 | 6/2000 |
| WO | WO01/21189 A1 | 3/2001 |
| WO | WO01/24810 A1 | 4/2001 |
| WO | WO02/00885 A2 | 1/2002 |
| WO | WO2004/080403 A2 | 9/2004 |
| WO | WO2006/069262 A2 | 6/2006 |
| WO | WO2006/078657 A2 | 7/2006 |
| WO | WO2006/128294 A1 | 12/2006 |
| WO | WO2007/066334 A1 | 6/2007 |
| WO | WO2007/091030 A2 | 8/2007 |
| WO | WO2008/039267 A2 | 4/2008 |
| WO | WO2009/016639 A2 | 2/2009 |
| WO | WO2009/026465 A2 | 2/2009 |

OTHER PUBLICATIONS

Chen et al., (1999) Enhanced protection against A lethal influenza virus challenge by immunization with both hemagglutinin- and neuraminidase-expresseing DNAs. Vaccine 17(7-8): 653-659.

Flechtner et al., (2006) High-affinity interactions between peptides and heat shock protein 70 augment CD8+ T lymphocyte immune responses. J immunol 177(2): 1017-1027.

Fournillier et al., (2006) Primary and memory T cell responses induced by hepatitis C virus multiepitope long peptides. Vaccine 24(16): 3153-3164.

Horimoto et al., (2004) Influenza A viruses possessing type B hemagglutinin and neuraminidase: potential as vaccine components. Microbes Infect 6(6): 579-583.

Jegerlehner et al., (2002) Regulation of IgG antibody responses by epitope density and CD21-mediated costimulation. Eur J Immunol 32(11): 3305-3314.

Jeon et al., (2002) Intranasal immunization with synthetic recombinant vaccine containing multiple epitopes of influenza virus. Vaccine 3214:1-9.

Lamb et al., (1985) Influenza virus M2 protein is an integral membrane protein expressed on the infected-cell surface. Cell 40(3): 627-633.

Levi and Arnon (1996) Synthetic recombinant influenza vaccine induces efficient long-term immunity and cross-strain protection, Vaccine 14(1): 85-92.

Liu et al., (2004) High epitope density in a single recombinant protein molecule of the extracellular domain of influenza A virus M2 protein significantly enhances protective immunity, Vaccine 23(3): 366-371.

Liu et al., (2005) Sequence comparison between the extracellular domain of M2 protein human and avian influenza A virus provides new information for bivalent influenza vaccine design. Microbes Infect 7(2): 171-177.

Otvos, XP009112218 (2008) Synthesis of a multivalent, multiepitope vaccine construct. Methods Mol Biol 494: 263-273.

Peek et al., (2008) Nanotechnology in vaccine delivery. Adv Drug Deliv Rev 60(8): 915-928.

Shapira et al., (1985) A synthetic vaccine against influenza with built-in adjuvanticity. Int J Immunopharmacol 7(5): 719-723.

Slepushkin et al., (1995) Protection of mice against influenza A virus challenge by vaccination with baculovirus-expressed M2 protein. Vaccine 13(15): 1399-1402.

Townsend and Skehel (1984) The influenza A virus nucleoprotein gene controls the induction of both subtype specific and cross-reactive cytotoxic T cells. J Exp Med 160(2): 552-563.

Yang et al., (2001) Multi-epitope schistosome vaccine candidates tested for protective immunogenicity in mice. Vaccine 19(1): 103-113.

Zou et al., (2005) The epitope recognized by a monoclonal antibody in influenza A virus M2 protein is immunogenic and confers immune protection. Int Immunopharmacol 5(4): 631-635.

Commitee for Proprietary Medicinal Products (CPMP) Note for Guidance on Harmonisation of Requirements for Influenza Vaccines (CPMP/BWP/214/96). 1997 (pp. 1-19).

Atsmon et al., (2014) Priming by a novel universal influenza vaccine (Multimeric-001)—A gateway for improving immune response in the elderly population. Vaccine. 32(44): 5816-5823.

Ben-Yedidia and Rudolph (2011) Development of a Universal Influenza Vaccine. BioProcess International 9(8)s: 46-49.

He et al., (2000) Calcium phosphate nanoparticle adjuvant. Clin Diagn Lab Immunol 7(6): 899-903.

Langer (1990) New methods of drug delivery. Science 249(4976): 1527-1533.

Li et al., (2003) Recombinant protein comprising multi-neutralizing epitopes induced high titer of antibodies against influenza A virus. Immunobiology 207(5): 305-13.

López et al., (1993) Leishmania mexicana promastigotes induce cytotoxic T lymphocytes in vivo that do not recognize infeed macrophages. Eur J Immunol 23(1): 217-23.

O'Hagan, et al., (1993) Long-term antibody responses in mice following subcutaneous immunization with ovalbumin entrapped in biodegradable microparticles. Vaccine 11(9): 965-969.

Wei et al., (2010) Induction of broadly neutralizing H1N1 influenza antibodies by vaccination. Science 329(5995): 1060-4.

* cited by examiner

```
                         SEQUENCE LISTING

<160> NUMBER OF SEQ ID NOS: 89

<210> SEQ ID NO 1
<211> LENGTH: 4
<212> TYPE: PRT
<213> ORGANISM: Artificial
<220> FEATURE:
<223> OTHER INFORMATION: Synthetic peptide

<400> SEQUENCE: 1

Glu Val Glu Thr
1

<210> SEQ ID NO 2
<211> LENGTH: 15
<212> TYPE: PRT
<213> ORGANISM: Artificial
<220> FEATURE:
<223> OTHER INFORMATION: Synthetic peptide

<400> SEQUENCE: 2

Met Ser Leu Leu Thr Glu Val Glu Thr His Thr Arg Asn Gly Trp
1               5                   10                  15

<210> SEQ ID NO 3
<211> LENGTH: 9
<212> TYPE: PRT
<213> ORGANISM: Artificial
<220> FEATURE:
<223> OTHER INFORMATION: Synthetic peptide

<400> SEQUENCE: 3

Pro Ile Arg Asn Glu Trp Gly Cys Arg
1               5

<210> SEQ ID NO 4
<211> LENGTH: 10
<212> TYPE: PRT
<213> ORGANISM: Artificial
<220> FEATURE:
<223> OTHER INFORMATION: Synthetic peptide

<400> SEQUENCE: 4

Glu Thr Pro Ile Arg Asn Glu Trp Gly Cys
1               5                   10

<210> SEQ ID NO 5
<211> LENGTH: 11
<212> TYPE: PRT
<213> ORGANISM: Artificial
<220> FEATURE:
<223> OTHER INFORMATION: Synthetic peptide
```

<400> SEQUENCE: 5

Pro Ile Arg Asn Glu Trp Gly Cys Arg Cys Asn
1               5                   10

<210> SEQ ID NO 6
<211> LENGTH: 9
<212> TYPE: PRT
<213> ORGANISM: Artificial
<220> FEATURE:
<223> OTHER INFORMATION: Synthetic peptide

<400> SEQUENCE: 6

Leu Leu Thr Glu Val Glu Thr Pro Ile
1               5

<210> SEQ ID NO 7
<211> LENGTH: 9
<212> TYPE: PRT
<213> ORGANISM: Artificial
<220> FEATURE:
<223> OTHER INFORMATION: Synthetic peptide

<400> SEQUENCE: 7

Ser Leu Leu Thr Glu Val Glu Thr Pro
1               5

<210> SEQ ID NO 8
<211> LENGTH: 10
<212> TYPE: PRT
<213> ORGANISM: Artificial
<220> FEATURE:
<223> OTHER INFORMATION: Synthetic peptide

<400> SEQUENCE: 8

Ser Leu Leu Thr Glu Val Glu Thr Pro Ile
1               5                   10

<210> SEQ ID NO 9
<211> LENGTH: 9
<212> TYPE: PRT
<213> ORGANISM: Artificial
<220> FEATURE:
<223> OTHER INFORMATION: Synthetic peptide

<400> SEQUENCE: 9

Leu Thr Glu Val Glu Thr Pro Leu Thr
1               5

<210> SEQ ID NO 10
<211> LENGTH: 15
<212> TYPE: PRT
<213> ORGANISM: Artificial
<220> FEATURE:
<223> OTHER INFORMATION: Synthetic peptide

<400> SEQUENCE: 10

Met Ser Leu Leu Thr Glu Val Glu Thr Pro Ile Arg Asn Glu Trp
1               5                   10                  15

<210> SEQ ID NO 11
<211> LENGTH: 18
<212> TYPE: PRT
<213> ORGANISM: Artificial
<220> FEATURE:
<223> OTHER INFORMATION: Synthetic peptide

```
<400> SEQUENCE: 11

Met Ser Leu Leu Thr Glu Val Glu Thr Pro Ile Arg Asn Glu Trp Gly
1               5                   10                  15

Cys Arg

<210> SEQ ID NO 12
<211> LENGTH: 15
<212> TYPE: PRT
<213> ORGANISM: Artificial
<220> FEATURE:
<223> OTHER INFORMATION: Synthetic peptide

<400> SEQUENCE: 12

Met Ser Leu Leu Thr Glu Val Glu Thr Leu Thr Lys Asn Gly Trp
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic peptide

<400> SEQUENCE: 13

Met Ser Leu Leu Thr Glu Val Glu Thr Leu Thr Arg Asn Gly Trp
1               5                   10                  15

<210> SEQ ID NO 14
<211> LENGTH: 9
<212> TYPE: PRT
<213> ORGANISM: Artificial
<220> FEATURE:
<223> OTHER INFORMATION: Synthetic peptide

<400> SEQUENCE: 14

Leu Thr Glu Val Glu Thr Pro Ile Arg
1               5

<210> SEQ ID NO 15
<211> LENGTH: 10
<212> TYPE: PRT
<213> ORGANISM: Artificial
<220> FEATURE:
<223> OTHER INFORMATION: Synthetic peptide

<400> SEQUENCE: 15

Leu Thr Glu Val Glu Thr Pro Ile Arg Asn
1               5                   10

<210> SEQ ID NO 16
<211> LENGTH: 9
<212> TYPE: PRT
<213> ORGANISM: Artificial
<220> FEATURE:
<223> OTHER INFORMATION: Synthetic peptide

<400> SEQUENCE: 16

Glu Val Glu Thr Pro Ile Arg Asn Glu
1               5

<210> SEQ ID NO 17
<211> LENGTH: 10
<212> TYPE: PRT
<213> ORGANISM: Artificial
<220> FEATURE:
<223> OTHER INFORMATION: Synthetic peptide
```

<400> SEQUENCE: 17

Glu Val Glu Thr Pro Ile Arg Asn Glu Trp
1               5                   10

<210> SEQ ID NO 18
<211> LENGTH: 11
<212> TYPE: PRT
<213> ORGANISM: Artificial
<220> FEATURE:
<223> OTHER INFORMATION: Synthetic peptide

<400> SEQUENCE: 18

Leu Thr Glu Val Glu Thr Pro Ile Arg Asn Glu
1               5                   10

<210> SEQ ID NO 19
<211> LENGTH: 15
<212> TYPE: PRT
<213> ORGANISM: Artificial
<220> FEATURE:
<223> OTHER INFORMATION: Synthetic peptide

<400> SEQUENCE: 19

Leu Thr Glu Val Glu Thr Pro Ile Arg Asn Glu Trp Gly Cys Arg
1               5                   10                  15

<210> SEQ ID NO 20
<211> LENGTH: 8
<212> TYPE: PRT
<213> ORGANISM: Artificial
<220> FEATURE:
<223> OTHER INFORMATION: Synthetic peptide

<400> SEQUENCE: 20

Glu Val Glu Thr Pro Ile Arg Asn
1               5

<210> SEQ ID NO 21
<211> LENGTH: 18
<212> TYPE: PRT
<213> ORGANISM: Artificial
<220> FEATURE:
<223> OTHER INFORMATION: Synthetic peptide

<400> SEQUENCE: 21

Met Ser Leu Leu Thr Glu Val Glu Thr Pro Thr Arg Asn Glu Trp Glu
1               5                   10                  15

Cys Arg

<210> SEQ ID NO 22
<211> LENGTH: 23
<212> TYPE: PRT
<213> ORGANISM: Artificial
<220> FEATURE:
<223> OTHER INFORMATION: Synthetic peptide

<400> SEQUENCE: 22

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 23
<211> LENGTH: 23

```
<212> TYPE: PRT
<213> ORGANISM: Artificial
<220> FEATURE:
<223> OTHER INFORMATION: Synthetic peptide

<400> SEQUENCE: 23

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 24
<211> LENGTH: 9
<212> TYPE: PRT
<213> ORGANISM: Artificial
<220> FEATURE:
<223> OTHER INFORMATION: Synthetic peptide

<400> SEQUENCE: 24

Val Glu Thr Pro Ile Arg Asn Glu Trp
1               5

<210> SEQ ID NO 25
<211> LENGTH: 11
<212> TYPE: PRT
<213> ORGANISM: Artificial
<220> FEATURE:
<223> OTHER INFORMATION: Synthetic peptide

<400> SEQUENCE: 25

Ser Leu Leu Thr Glu Val Glu Thr Tyr Val Leu
1               5                   10

<210> SEQ ID NO 26
<211> LENGTH: 11
<212> TYPE: PRT
<213> ORGANISM: Artificial
<220> FEATURE:
<223> OTHER INFORMATION: Synthetic peptide

<400> SEQUENCE: 26

Ser Leu Leu Thr Glu Val Glu Thr Tyr Val Pro
1               5                   10

<210> SEQ ID NO 27
<211> LENGTH: 9
<212> TYPE: PRT
<213> ORGANISM: Artificial
<220> FEATURE:
<223> OTHER INFORMATION: Synthetic peptide

<400> SEQUENCE: 27

Leu Leu Thr Glu Val Glu Thr Tyr Val
1               5

<210> SEQ ID NO 28
<211> LENGTH: 8
<212> TYPE: PRT
<213> ORGANISM: Artificial
<220> FEATURE:
<223> OTHER INFORMATION: Synthetic peptide

<400> SEQUENCE: 28

Ser Ile Val Pro Ser Gly Pro Leu
1               5
```

<210> SEQ ID NO 29
<211> LENGTH: 15
<212> TYPE: PRT
<213> ORGANISM: Artificial
<220> FEATURE:
<223> OTHER INFORMATION: Synthetic peptide

<400> SEQUENCE: 29

Ser Gly Pro Leu Lys Ala Glu Ile Ala Gln Arg Leu Glu Asp Val
1               5                   10                  15

<210> SEQ ID NO 30
<211> LENGTH: 12
<212> TYPE: PRT
<213> ORGANISM: Artificial
<220> FEATURE:
<223> OTHER INFORMATION: Synthetic peptide

<400> SEQUENCE: 30

Gly Pro Leu Lys Ala Glu Ile Ala Gln Arg Leu Glu
1               5                   10

<210> SEQ ID NO 31
<211> LENGTH: 9
<212> TYPE: PRT
<213> ORGANISM: Artificial
<220> FEATURE:
<223> OTHER INFORMATION: Synthetic peptide

<400> SEQUENCE: 31

Arg Leu Glu Asp Val Phe Ala Gly Lys
1               5

<210> SEQ ID NO 32
<211> LENGTH: 11
<212> TYPE: PRT
<213> ORGANISM: Artificial
<220> FEATURE:
<223> OTHER INFORMATION: Synthetic peptide

<400> SEQUENCE: 32

Ala Leu Met Glu Trp Leu Lys Thr Arg Pro Ile
1               5                   10

<210> SEQ ID NO 33
<211> LENGTH: 10
<212> TYPE: PRT
<213> ORGANISM: Artificial
<220> FEATURE:
<223> OTHER INFORMATION: Synthetic peptide

<400> SEQUENCE: 33

Pro Ile Leu Ser Pro Leu Thr Lys Gly Ile
1               5                   10

<210> SEQ ID NO 34
<211> LENGTH: 9
<212> TYPE: PRT
<213> ORGANISM: Artificial
<220> FEATURE:
<223> OTHER INFORMATION: Synthetic peptide

<400> SEQUENCE: 34

Ile Leu Ser Pro Leu Thr Lys Gly Ile
1               5

<210> SEQ ID NO 35

```
<211> LENGTH: 19
<212> TYPE: PRT
<213> ORGANISM: Artificial
<220> FEATURE:
<223> OTHER INFORMATION: Synthetic peptide

<400> SEQUENCE: 35

Leu Thr Lys Gly Ile Leu Gly Phe Val Phe Thr Leu Thr Val Pro Ser
1               5                   10                  15
Glu Arg Gly

<210> SEQ ID NO 36
<211> LENGTH: 13
<212> TYPE: PRT
<213> ORGANISM: Artificial
<220> FEATURE:
<223> OTHER INFORMATION: Synthetic peptide

<400> SEQUENCE: 36

Thr Lys Gly Ile Leu Gly Phe Val Phe Thr Leu Thr Val
1               5                   10

<210> SEQ ID NO 37
<211> LENGTH: 12
<212> TYPE: PRT
<213> ORGANISM: Artificial
<220> FEATURE:
<223> OTHER INFORMATION: Synthetic peptide

<400> SEQUENCE: 37

Lys Gly Ile Leu Gly Phe Val Phe Thr Leu Thr Val
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Gly Ile Leu Gly Phe Val Phe Thr Leu
1               5

<210> SEQ ID NO 39
<211> LENGTH: 9
<212> TYPE: PRT
<213> ORGANISM: Artificial
<220> FEATURE:
<223> OTHER INFORMATION: Synthetic peptide

<400> SEQUENCE: 39

Leu Gly Phe Val Phe Thr Leu Thr Val
1               5

<210> SEQ ID NO 40
<211> LENGTH: 9
<212> TYPE: PRT
<213> ORGANISM: Artificial
<220> FEATURE:
<223> OTHER INFORMATION: Synthetic peptide

<400> SEQUENCE: 40

Ile Leu Gly Phe Val Phe Thr Leu Thr
1               5
```

-continued

```
<210> SEQ ID NO 41
<211> LENGTH: 8
<212> TYPE: PRT
<213> ORGANISM: Artificial
<220> FEATURE:
<223> OTHER INFORMATION: Synthetic peptide

<400> SEQUENCE: 41

Ala Ser Cys Met Gly Leu Ile Tyr
1               5

<210> SEQ ID NO 42
<211> LENGTH: 9
<212> TYPE: PRT
<213> ORGANISM: Artificial
<220> FEATURE:
<223> OTHER INFORMATION: Synthetic peptide

<400> SEQUENCE: 42

Arg Met Gly Ala Val Thr Thr Glu Val
1               5

<210> SEQ ID NO 43
<211> LENGTH: 11
<212> TYPE: PRT
<213> ORGANISM: Artificial
<220> FEATURE:
<223> OTHER INFORMATION: Synthetic peptide

<400> SEQUENCE: 43

Gly Leu Val Cys Ala Thr Cys Glu Gln Ile Ala
1               5                   10

<210> SEQ ID NO 44
<211> LENGTH: 9
<212> TYPE: PRT
<213> ORGANISM: Artificial
<220> FEATURE:
<223> OTHER INFORMATION: Synthetic peptide

<400> SEQUENCE: 44

Gln Met Val Ala Thr Thr Asn Pro Leu
1               5

<210> SEQ ID NO 45
<211> LENGTH: 10
<212> TYPE: PRT
<213> ORGANISM: Artificial
<220> FEATURE:
<223> OTHER INFORMATION: Synthetic peptide

<400> SEQUENCE: 45

Gln Met Val Ala Thr Thr Asn Pro Leu Ile
1               5                   10

<210> SEQ ID NO 46
<211> LENGTH: 10
<212> TYPE: PRT
<213> ORGANISM: Artificial
<220> FEATURE:
<223> OTHER INFORMATION: Synthetic peptide

<400> SEQUENCE: 46

Arg Met Val Leu Ala Ser Thr Thr Ala Lys
1               5                   10

<210> SEQ ID NO 47
```

```
<211> LENGTH: 9
<212> TYPE: PRT
<213> ORGANISM: Artificial
<220> FEATURE:
<223> OTHER INFORMATION: Synthetic peptide

<400> SEQUENCE: 47

Asp Leu Leu Glu Asn Leu Glu Thr Tyr
1               5

<210> SEQ ID NO 48
<211> LENGTH: 18
<212> TYPE: PRT
<213> ORGANISM: Artificial
<220> FEATURE:
<223> OTHER INFORMATION: Synthetic peptide

<400> SEQUENCE: 48

Ser Lys Ala Tyr Ser Asn Cys Tyr Pro Tyr Asp Val Pro Asp Tyr Ala
1               5                   10                  15

Ser Leu

<210> SEQ ID NO 49
<211> LENGTH: 18
<212> TYPE: PRT
<213> ORGANISM: Artificial
<220> FEATURE:
<223> OTHER INFORMATION: Synthetic peptide

<400> SEQUENCE: 49

Ser Lys Ala Phe Ser Asn Cys Tyr Pro Tyr Asp Val Pro Asp Tyr Ala
1               5                   10                  15

Ser Leu

<210> SEQ ID NO 50
<211> LENGTH: 18
<212> TYPE: PRT
<213> ORGANISM: Artificial
<220> FEATURE:
<223> OTHER INFORMATION: Synthetic peptide

<400> SEQUENCE: 50

Ser Thr Ala Tyr Ser Asn Cys Tyr Pro Tyr Asp Val Pro Asp Tyr Ala
1               5                   10                  15

Ser Leu

<210> SEQ ID NO 51
<211> LENGTH: 7
<212> TYPE: PRT
<213> ORGANISM: Artificial
<220> FEATURE:
<223> OTHER INFORMATION: Synthetic peptide

<400> SEQUENCE: 51

Trp Thr Gly Val Thr Gln Asn
1               5

<210> SEQ ID NO 52
<211> LENGTH: 10
<212> TYPE: PRT
<213> ORGANISM: Artificial
<220> FEATURE:
<223> OTHER INFORMATION: Synthetic peptide

<400> SEQUENCE: 52
```

```
Trp Leu Thr Gly Lys Asn Gly Leu Tyr Pro
1               5                   10
```

<210> SEQ ID NO 53
<211> LENGTH: 10
<212> TYPE: PRT
<213> ORGANISM: Artificial
<220> FEATURE:
<223> OTHER INFORMATION: Synthetic peptide

<400> SEQUENCE: 53

```
Trp Leu Thr Glu Lys Glu Gly Ser Tyr Pro
1               5                   10
```

<210> SEQ ID NO 54
<211> LENGTH: 19
<212> TYPE: PRT
<213> ORGANISM: Artificial
<220> FEATURE:
<223> OTHER INFORMATION: Synthetic peptide

<400> SEQUENCE: 54

```
Pro Lys Tyr Val Lys Gln Asn Thr Leu Lys Leu Ala Thr Gly Met Arg
1               5                   10                  15

Asn Val Pro
```

<210> SEQ ID NO 55
<211> LENGTH: 11
<212> TYPE: PRT
<213> ORGANISM: Artificial
<220> FEATURE:
<223> OTHER INFORMATION: Synthetic peptide

<400> SEQUENCE: 55

```
Gly Val Lys Leu Glu Ser Met Gly Ile Tyr Gln
1               5                   10
```

<210> SEQ ID NO 56
<211> LENGTH: 11
<212> TYPE: PRT
<213> ORGANISM: Artificial
<220> FEATURE:
<223> OTHER INFORMATION: Synthetic peptide

<400> SEQUENCE: 56

```
Glu Ile Ser Gly Val Lys Leu Glu Ser Met Gly
1               5                   10
```

<210> SEQ ID NO 57
<211> LENGTH: 10
<212> TYPE: PRT
<213> ORGANISM: Artificial
<220> FEATURE:
<223> OTHER INFORMATION: Synthetic peptide

<400> SEQUENCE: 57

```
Asn Val Lys Asn Leu Tyr Glu Lys Val Lys
1               5                   10
```

<210> SEQ ID NO 58
<211> LENGTH: 18
<212> TYPE: PRT
<213> ORGANISM: Artificial
<220> FEATURE:
<223> OTHER INFORMATION: Synthetic peptide

<400> SEQUENCE: 58

```
Lys Val Lys Ile Leu Pro Lys Asp Arg Trp Thr Gln His Thr Thr Thr
1               5                   10                  15

Gly Gly

<210> SEQ ID NO 59
<211> LENGTH: 13
<212> TYPE: PRT
<213> ORGANISM: Artificial
<220> FEATURE:
<223> OTHER INFORMATION: Synthetic peptide

<400> SEQUENCE: 59

Pro Lys Tyr Val Lys Gln Asn Thr Leu Lys Leu Ala Thr
1               5                   10

<210> SEQ ID NO 60
<211> LENGTH: 9
<212> TYPE: PRT
<213> ORGANISM: Artificial
<220> FEATURE:
<223> OTHER INFORMATION: Synthetic peptide

<400> SEQUENCE: 60

Lys Thr Gly Gly Pro Ile Tyr Arg Arg
1               5

<210> SEQ ID NO 61
<211> LENGTH: 9
<212> TYPE: PRT
<213> ORGANISM: Artificial
<220> FEATURE:
<223> OTHER INFORMATION: Synthetic peptide

<400> SEQUENCE: 61

Cys Thr Glu Leu Lys Leu Ser Asp Tyr
1               5

<210> SEQ ID NO 62
<211> LENGTH: 14
<212> TYPE: PRT
<213> ORGANISM: Artificial
<220> FEATURE:
<223> OTHER INFORMATION: Synthetic peptide

<400> SEQUENCE: 62

His Pro Ser Ala Gly Lys Asp Pro Lys Lys Thr Gly Gly Pro
1               5                   10

<210> SEQ ID NO 63
<211> LENGTH: 13
<212> TYPE: PRT
<213> ORGANISM: Artificial
<220> FEATURE:
<223> OTHER INFORMATION: Synthetic peptide

<400> SEQUENCE: 63

His Pro Ser Ala Gly Lys Asp Pro Lys Lys Thr Gly Gly
1               5                   10

<210> SEQ ID NO 64
<211> LENGTH: 24
<212> TYPE: PRT
<213> ORGANISM: Artificial
<220> FEATURE:
<223> OTHER INFORMATION: Synthetic peptide
```

```
<400> SEQUENCE: 64

Phe Trp Arg Gly Glu Asn Gly Arg Lys Thr Arg Ser Ala Tyr Glu Arg
1               5                   10                  15

Met Cys Asn Ile Leu Lys Gly Lys
            20

<210> SEQ ID NO 65
<211> LENGTH: 9
<212> TYPE: PRT
<213> ORGANISM: Artificial
<220> FEATURE:
<223> OTHER INFORMATION: Synthetic peptide

<400> SEQUENCE: 65

Ile Leu Arg Gly Ser Val Ala His Lys
1               5

<210> SEQ ID NO 66
<211> LENGTH: 8
<212> TYPE: PRT
<213> ORGANISM: Artificial
<220> FEATURE:
<223> OTHER INFORMATION: Synthetic peptide

<400> SEQUENCE: 66

Lys Leu Leu Gln Asn Ser Gln Tyr
1               5

<210> SEQ ID NO 67
<211> LENGTH: 15
<212> TYPE: PRT
<213> ORGANISM: Artificial
<220> FEATURE:
<223> OTHER INFORMATION: Synthetic peptide

<400> SEQUENCE: 67

Ser Ala Ala Phe Glu Asp Leu Arg Val Leu Ser Phe Ile Arg Gly
1               5                   10                  15

<210> SEQ ID NO 68
<211> LENGTH: 16
<212> TYPE: PRT
<213> ORGANISM: Artificial
<220> FEATURE:
<223> OTHER INFORMATION: Synthetic peptide

<400> SEQUENCE: 68

Ser Ala Ala Phe Glu Asp Leu Arg Val Ser Ser Phe Ile Arg Gly Thr
1               5                   10                  15

<210> SEQ ID NO 69
<211> LENGTH: 16
<212> TYPE: PRT
<213> ORGANISM: Artificial
<220> FEATURE:
<223> OTHER INFORMATION: Synthetic peptide

<400> SEQUENCE: 69

Ser Ala Ala Phe Glu Asp Leu Arg Val Leu Ser Phe Ile Arg Gly Tyr
1               5                   10                  15

<210> SEQ ID NO 70
<211> LENGTH: 14
<212> TYPE: PRT
<213> ORGANISM: Artificial
<220> FEATURE:
```

```
<223> OTHER INFORMATION: Synthetic peptide

<400> SEQUENCE: 70

Glu Leu Arg Ser Arg Tyr Trp Ala Ile Arg Thr Arg Ser Gly
1               5                   10

<210> SEQ ID NO 71
<211> LENGTH: 9
<212> TYPE: PRT
<213> ORGANISM: Artificial
<220> FEATURE:
<223> OTHER INFORMATION: Synthetic peptide

<400> SEQUENCE: 71

Glu Leu Arg Ser Arg Tyr Trp Ala Ile
1               5

<210> SEQ ID NO 72
<211> LENGTH: 9
<212> TYPE: PRT
<213> ORGANISM: Artificial
<220> FEATURE:
<223> OTHER INFORMATION: Synthetic peptide

<400> SEQUENCE: 72

Ser Arg Tyr Trp Ala Ile Arg Thr Arg
1               5

<210> SEQ ID NO 73
<211> LENGTH: 10
<212> TYPE: PRT
<213> ORGANISM: Artificial
<220> FEATURE:
<223> OTHER INFORMATION: Synthetic peptide

<400> SEQUENCE: 73

Tyr Trp Ala Ile Arg Thr Arg Ser Gly Gly
1               5                   10

<210> SEQ ID NO 74
<211> LENGTH: 9
<212> TYPE: PRT
<213> ORGANISM: Artificial
<220> FEATURE:
<223> OTHER INFORMATION: Synthetic peptide

<400> SEQUENCE: 74

Ser Arg Tyr Trp Ala Ile Arg Thr Arg
1               5

<210> SEQ ID NO 75
<211> LENGTH: 9
<212> TYPE: PRT
<213> ORGANISM: Artificial
<220> FEATURE:
<223> OTHER INFORMATION: Synthetic peptide

<400> SEQUENCE: 75

Leu Pro Phe Asp Lys Pro Thr Ile Met
1               5

<210> SEQ ID NO 76
<211> LENGTH: 9
<212> TYPE: PRT
<213> ORGANISM: Artificial
<220> FEATURE:
<223> OTHER INFORMATION: Synthetic peptide
```

<400> SEQUENCE: 76

Val Ser Asp Gly Gly Pro Asn Leu Tyr
1               5

<210> SEQ ID NO 77
<211> LENGTH: 9
<212> TYPE: PRT
<213> ORGANISM: Artificial
<220> FEATURE:
<223> OTHER INFORMATION: Synthetic peptide

<400> SEQUENCE: 77

Arg Arg Ser Phe Glu Leu Lys Lys Leu
1               5

<210> SEQ ID NO 78
<211> LENGTH: 9
<212> TYPE: PRT
<213> ORGANISM: Artificial
<220> FEATURE:
<223> OTHER INFORMATION: Synthetic peptide

<400> SEQUENCE: 78

Arg Arg Ala Thr Ala Ile Leu Arg Lys
1               5

<210> SEQ ID NO 79
<211> LENGTH: 9
<212> TYPE: PRT
<213> ORGANISM: Artificial
<220> FEATURE:
<223> OTHER INFORMATION: Synthetic peptide

<400> SEQUENCE: 79

Arg Pro Ile Ile Arg Pro Ala Thr Leu
1               5

<210> SEQ ID NO 80
<211> LENGTH: 9
<212> TYPE: PRT
<213> ORGANISM: Artificial
<220> FEATURE:
<223> OTHER INFORMATION: Synthetic peptide

<400> SEQUENCE: 80

Ala Asp Arg Gly Leu Leu Arg Asp Ile
1               5

<210> SEQ ID NO 81
<211> LENGTH: 13
<212> TYPE: PRT
<213> ORGANISM: Artificial
<220> FEATURE:
<223> OTHER INFORMATION: Synthetic peptide

<400> SEQUENCE: 81

Pro Tyr Tyr Thr Gly Glu His Ala Lys Ala Ile Gly Asn
1               5                   10

<210> SEQ ID NO 82
<211> LENGTH: 19
<212> TYPE: PRT
<213> ORGANISM: Artificial
<220> FEATURE:
<223> OTHER INFORMATION: Synthetic peptide

<400> SEQUENCE: 82

Pro Ala Lys Leu Leu Lys Glu Arg Gly Phe Phe Gly Ala Ile Ala Gly
1               5                   10                  15

Phe Leu Glu

<210> SEQ ID NO 83
<211> LENGTH: 2199
<212> TYPE: DNA
<213> ORGANISM: Artificial
<220> FEATURE:
<223> OTHER INFORMATION: Synthetic polynucleotide

<400> SEQUENCE: 83

```
atgcatatga gatctccagc taaacttctg aaagaacgtg attttttcgg tgcaatcgct      60
ggttttctgg aggggtcgaa agcctacagt aactgttacc cctacgatgt gcccgattat     120
gccagcctgg gtagcctcct tacagaagtt gaaacttatg tgctcggctg gctgacaggg     180
aaaaacggcc tttatcctgt gtggaccggc gtgacgcaga acggattctg gcgtggcgaa     240
aatggacgta aaactcgcag tgcgtatgag cgcatgtgta catcctcaa aggtaaaggc     300
ccgaaatatg tgaaacagaa tacattaaaa ttagccaccg cgcgagcgc tgcctttgaa     360
gacctccgtg tgctcagttt tatccgcggt tatggggaac tgcgttctcg ctattgggcg     420
atccgtaccc ggtcagggg tccaccggcg aagctgctga agaacgtgg gttcttcggt     480
gcgattgccg gtttcttgga aggatcaaaa gcgtattcga actgctaccc gtatgatgtg     540
ccagattacg ccagcctggg ctccctcttg acagaggtcg aaacctatgt actgggttgg     600
ctgaccggta agaacggtct gtatccggtt tggactggtg tgacacaaaa cggcttttgg     660
cgggggaaa acggccggaa aacccgcagc gcttacgagc gcatgtgcaa cattctgaaa     720
ggcaaaggcc gaaatacgt gaagcagaat acgctcaaac ttgccacggg cgcaagcgca     780
gcctttgaag acctgcgggt cttgagcttt atccgcggtt acggggagct gcggtcgcgc     840
tactgggcga ttcgtacgcg tagtggtgga cctcccgcga acttctgaa agagcggggc     900
ttctttggag cgattgcggg cttcttggag ggaagcaaag ggaagcaaag cctactctaa     960
tacgatgtgc ctgattatgc gagcctcggt agcttgctga cagaagtgga aacctacgtt    1020
ctcggctggc tgacgggcaa aaatggtctc tacccagtgt ggaccggagt acccagaat    1080
gggttctggc gcggtgagaa cggccgtaaa acacgttcag cgtacgagcg gatgtgcaac    1140
atcttaaaag gcaaaggacc gaaatacgtc aagcagaata tctctgaagtt agccactggg    1200
gcctcagccg cctttgaaga ccttcgcgtc ttgagtttta tccggggtta tggggaactg    1260
cggagccgct actgggctat tcgtacgcgg tcgggtggcc cactcgagcc ggccaaattg    1320
ctcaaagaac gtggtttctt cggagcgatc gcaggtttc ttgaaggctc taaagcgtac    1380
agcaactgtt atccatacga tgtgccggat tacgccagtc tgggttccct cctgaccgag    1440
gtggaaacgt atgtactagg atggctcacg ggtaaaaatg gtctctatcc tgtgtggacg    1500
ggcgtaaccc agaacggctt tggcggggc gaaaacggcc gcaaacccg tagcgcatac    1560
gagcgtatgt gtaacatcct taaaggcaaa ggtccaaaat acgttaagca gaatacccctg    1620
aaactggcta cgggcgccag tgcggccttc gaagatttac gggtgctgtc cttcatccgc    1680
ggctatggtg aactgcgctc tcgttactgg gcaatccgta cccgcagtgg cggacctccg    1740
gctaaactgt tgaagaacg cggcttcttt ggtgctatcg caggttttct ggaaggaagt    1800
aaagcatatt cgaattgtta tccctacgac gtgccggatt atgcgtcgct cggttcgctg    1860
```

-continued

```
ctgaccgagg tggaaaccta cgttctaggc tggttgacag gtaagaacgg gctttacccg    1920
gtatggaccg cgttaccca gaacggtttt tggcgcggtg aaaatggccg taaaactcgg    1980
tcagcatacg aacggatgtg caatatcttg aaaggtaaag gaccgaaata cgttaaacag    2040
aacacgctga aactggcaac aggcgccagc gcggcgtttg aggatttacg cgtcctgtca    2100
tttattcggg gctacggcga attacgtagt cgttattggg cgattcgtac ccgcagcgga    2160
gggctcgagt aataaaagct ttctagacat atgatgcat                            2199
```

<210> SEQ ID NO 84
<211> LENGTH: 723
<212> TYPE: PRT
<213> ORGANISM: Artificial
<220> FEATURE:
<223> OTHER INFORMATION: Synthetic peptide

<400> SEQUENCE: 84

```
Met His Met Arg Ser Pro Ala Lys Leu Leu Lys Glu Arg Gly Phe Phe
1               5                   10                  15

Gly Ala Ile Ala Gly Phe Leu Glu Gly Ser Lys Ala Tyr Ser Asn Cys
            20                  25                  30

Tyr Pro Tyr Asp Val Pro Asp Tyr Ala Ser Leu Gly Ser Leu Leu Thr
        35                  40                  45

Glu Val Glu Thr Tyr Val Leu Gly Trp Leu Thr Gly Lys Asn Gly Leu
    50                  55                  60

Tyr Pro Val Trp Thr Gly Val Thr Gln Asn Gly Phe Trp Arg Gly Glu
65                  70                  75                  80

Asn Gly Arg Lys Thr Arg Ser Ala Tyr Glu Arg Met Cys Asn Ile Leu
                85                  90                  95

Lys Gly Lys Gly Pro Lys Tyr Val Lys Gln Asn Thr Leu Lys Leu Ala
            100                 105                 110

Thr Gly Ala Ser Ala Ala Phe Glu Asp Leu Arg Val Leu Ser Phe Ile
        115                 120                 125

Arg Gly Tyr Gly Glu Leu Arg Ser Arg Tyr Trp Ala Ile Arg Thr Arg
    130                 135                 140

Ser Gly Gly Pro Pro Ala Lys Leu Leu Lys Glu Arg Gly Phe Phe Gly
145                 150                 155                 160

Ala Ile Ala Gly Phe Leu Glu Gly Ser Lys Ala Tyr Ser Asn Cys Tyr
                165                 170                 175

Pro Tyr Asp Val Pro Asp Tyr Ala Ser Leu Gly Ser Leu Leu Thr Glu
            180                 185                 190

Val Glu Thr Tyr Val Leu Gly Thr Leu Thr Gly Lys Asn Gly Leu Tyr
        195                 200                 205

Pro Val Trp Thr Gly Val Thr Gln Asn Gly Phe Trp Arg Gly Glu Asn
    210                 215                 220

Gly Arg Lys Thr Arg Ser Ala Tyr Glu Arg Met Cys Asn Ile Leu Lys
225                 230                 235                 240

Gly Lys Gly Pro Lys Tyr Val Lys Gln Asn Thr Leu Lys Leu Ala Thr
                245                 250                 255

Gly Ala Ser Ala Ala Phe Glu Asp Leu Arg Val Leu Ser Phe Ile Arg
            260                 265                 270

Gly Tyr Gly Glu Leu Arg Ser Arg Tyr Trp Ala Ile Arg Thr Arg Ser
        275                 280                 285

Gly Gly Pro Pro Ala Lys Leu Leu Lys Glu Arg Gly Phe Phe Gly Ala
    290                 295                 300
```

-continued

```
Ile Ala Gly Phe Leu Glu Gly Ser Lys Ala Tyr Ser Asn Cys Tyr Pro
305                 310                 315                 320

Tyr Asp Val Pro Asp Tyr Ala Ser Leu Gly Ser Leu Leu Thr Glu Val
            325                 330                 335

Glu Thr Tyr Val Leu Gly Trp Leu Thr Gly Lys Asn Gly Leu Tyr Pro
                340                 345                 350

Val Trp Thr Gly Val Thr Gln Asn Gly Phe Trp Arg Gly Glu Asn Gly
            355                 360                 365

Arg Lys Thr Arg Ser Ala Tyr Glu Arg Met Cys Asn Ile Leu Lys Gly
        370                 375                 380

Lys Gly Pro Lys Tyr Val Lys Gln Asn Thr Leu Lys Leu Ala Thr Gly
385                 390                 395                 400

Ala Ser Ala Ala Phe Glu Asp Leu Arg Val Leu Ser Phe Ile Arg Gly
                405                 410                 415

Tyr Gly Glu Leu Arg Ser Arg Tyr Trp Ala Ile Arg Thr Arg Ser Gly
            420                 425                 430

Gly Pro Leu Glu Pro Ala Lys Leu Leu Lys Glu Arg Gly Phe Phe Gly
        435                 440                 445

Ala Ile Ala Gly Phe Leu Glu Gly Ser Lys Ala Tyr Ser Asn Cys Tyr
450                 455                 460

Pro Tyr Asp Val Pro Asp Tyr Ala Ser Leu Gly Ser Leu Leu Thr Glu
465                 470                 475                 480

Val Glu Thr Tyr Val Leu Gly Trp Leu Thr Gly Lys Asn Gly Leu Tyr
                485                 490                 495

Pro Val Trp Thr Gly Val Thr Gln Asn Gly Phe Trp Arg Gly Glu Asn
            500                 505                 510

Gly Arg Lys Thr Arg Ser Ala Tyr Glu Arg Met Cys Asn Ile Leu Lys
        515                 520                 525

Gly Lys Gly Pro Lys Tyr Val Lys Gln Asn Thr Leu Lys Leu Ala Thr
    530                 535                 540

Gly Ala Ser Ala Ala Phe Glu Asp Leu Arg Val Leu Ser Phe Ile Arg
545                 550                 555                 560

Gly Tyr Gly Glu Leu Arg Ser Arg Tyr Trp Ala Ile Arg Thr Arg Ser
                565                 570                 575

Gly Gly Pro Pro Ala Lys Leu Leu Lys Glu Arg Gly Phe Phe Gly Ala
            580                 585                 590

Ile Ala Gly Phe Leu Glu Gly Ser Lys Ala Tyr Ser Asn Cys Tyr Pro
        595                 600                 605

Tyr Asp Val Pro Asp Tyr Ala Ser Leu Gly Ser Leu Leu Thr Glu Val
    610                 615                 620

Glu Thr Tyr Val Leu Gly Trp Leu Thr Gly Lys Asn Gly Leu Tyr Pro
625                 630                 635                 640

Val Trp Thr Gly Val Thr Gln Asn Gly Phe Trp Arg Gly Glu Asn Gly
                645                 650                 655

Arg Lys Thr Arg Ser Ala Tyr Glu Arg Met Cys Asn Ile Leu Lys Gly
            660                 665                 670

Lys Gly Pro Lys Tyr Val Lys Gln Asn Thr Leu Lys Leu Ala Thr Gly
        675                 680                 685

Ala Ser Ala Ala Phe Glu Asp Leu Arg Val Leu Ser Phe Ile Arg Gly
    690                 695                 700

Tyr Gly Glu Leu Arg Ser Arg Tyr Trp Ala Ile Arg Thr Arg Ser Gly
705                 710                 715                 720

Gly Leu Glu
```

<210> SEQ ID NO 85
<211> LENGTH: 1299
<212> TYPE: DNA
<213> ORGANISM: Artificial
<220> FEATURE:
<223> OTHER INFORMATION: Synthetic polynucleotide

<400> SEQUENCE: 85

```
atgcatatga gatctccagc taaacttctg aaagaacgtg gattttttcgg tgcaatcgct      60
ggttttctgg agccaccggc gaagctgctg aaagaacgtg ggttcttcgg tgcgattgcc     120
ggtttcttgg aacctcccgc gaaacttctg aaagagcggg gcttctttgg agcgattgcg     180
ggcttcttgg agccatcgaa agcctacagt aactgttacc cctacgatgt gcccgattat     240
gccagcctgc cttcaaaagc gtattcgaac tgctacccgt atgatgtgcc agattacgcc     300
agcctgccaa gcaaagccta ctctaattgt tacccatacg atgtgcctga ttatgcgagc     360
ctccctagcc tccttacaga agttgaaact tatgtgctca gcttgctgac agaagtggaa     420
acctacgttc tcagcttgct gacagaagtg gaaacctacg ttctctggct gacagggaaa     480
aacggccttt atccttggct gaccggtaag aacggtctgt atccgtggct gacgggcaaa     540
aatggtctct acccatggac cggcgtgacg cagaaccctt ggactggtgt gacacaaaac     600
ccatggaccg gagttaccca gaatcctttc tggcgtggcg aaaatggacg taaaactcgc     660
agtgcgtatg agcgcatgtg taacatcctc aaaggtaaac ccttttggcg ggggaaaac     720
ggccggaaaa cccgcagcgc ttacgagcgc atgtgcaaca ttctgaaagg caaaccattc     780
tggcgcggtg agaacggccg taaaacacgt tcagcgtacg agcggatgtg caacatctta     840
aaaggcaaac tccgaaata cgtgaagcag aatacgctca atacgtcaa gcagaatact     900
tacgtcaagc agaatactct gaagttagcc actccgccga atacgtcaa gcagaatact     960
ctgaagttag ccactccttc agccgccttt gaagacttc gcgtcttgag ttttatccgg    1020
ggttatccaa gcgcagcctt tgaagacctg cgggtcttga gctttatccg cggttaccct    1080
tcagccgcct ttgaagacct tcgcgtcttg agttttatcc ggggttatcc agaactgcgt    1140
tctcgctatt gggcgatccg tacccggtca gggccggagc tgcggtcgcg ctactgggcg    1200
attcgtacgc gtagtggtcc agaactgcgg agccgctact gggctattcg tacgcggtcg    1260
ggttaataac tcgagaggct ttctagacat atgatgcat                             1299
```

<210> SEQ ID NO 86
<211> LENGTH: 421
<212> TYPE: PRT
<213> ORGANISM: Artificial
<220> FEATURE:
<223> OTHER INFORMATION: Synthetic peptide

<400> SEQUENCE: 86

```
Met His Met Arg Ser Pro Ala Lys Leu Leu Lys Glu Arg Gly Phe Phe
1               5                   10                  15

Gly Ala Ile Ala Gly Phe Leu Glu Pro Pro Ala Lys Leu Leu Lys Glu
                20                  25                  30

Arg Gly Phe Phe Gly Ala Ile Ala Gly Phe Leu Glu Pro Pro Ala Lys
            35                  40                  45

Leu Leu Lys Glu Arg Gly Phe Phe Gly Ala Ile Ala Gly Phe Leu Glu
        50                  55                  60

Pro Ser Lys Ala Tyr Ser Asn Cys Tyr Pro Tyr Asp Val Pro Asp Tyr
65                  70                  75                  80
```

Ala Ser Leu Pro Ser Lys Ala Tyr Ser Asn Cys Tyr Pro Tyr Asp Val
                85                  90                  95

Pro Asp Tyr Ala Ser Leu Pro Ser Lys Ala Tyr Ser Asn Cys Tyr Pro
            100                 105                 110

Tyr Asp Val Pro Asp Tyr Ala Ser Leu Pro Ser Leu Leu Thr Glu Val
        115                 120                 125

Glu Thr Tyr Val Leu Ser Leu Leu Thr Glu Val Glu Thr Tyr Val Leu
130                 135                 140

Ser Leu Leu Thr Glu Val Glu Thr Tyr Val Leu Trp Leu Thr Gly Lys
145                 150                 155                 160

Asn Gly Leu Tyr Pro Trp Leu Thr Gly Lys Asn Gly Leu Tyr Pro Trp
                165                 170                 175

Leu Thr Gly Lys Asn Gly Leu Tyr Pro Trp Thr Gly Val Thr Gln Asn
            180                 185                 190

Pro Trp Thr Gly Val Thr Gln Asn Pro Trp Thr Gly Val Thr Gln Asn
        195                 200                 205

Pro Phe Trp Arg Gly Glu Asn Gly Arg Lys Thr Arg Ser Ala Tyr Glu
    210                 215                 220

Arg Met Cys Asn Ile Leu Lys Gly Lys Pro Phe Trp Arg Gly Glu Asn
225                 230                 235                 240

Gly Arg Lys Thr Arg Ser Ala Tyr Glu Arg Met Cys Asn Ile Leu Lys
                245                 250                 255

Gly Lys Pro Phe Trp Arg Gly Glu Asn Gly Arg Lys Thr Arg Ser Ala
            260                 265                 270

Tyr Glu Arg Met Cys Asn Ile Leu Lys Gly Lys Pro Pro Lys Tyr Val
        275                 280                 285

Lys Gln Asn Thr Leu Lys Leu Ala Thr Pro Pro Lys Tyr Val Lys Gln
    290                 295                 300

Asn Thr Leu Lys Leu Ala Thr Pro Pro Lys Tyr Val Lys Gln Asn Thr
305                 310                 315                 320

Leu Lys Leu Ala Thr Pro Ser Ala Ala Phe Glu Asp Leu Arg Val Leu
                325                 330                 335

Ser Phe Ile Arg Gly Tyr Pro Ser Ala Ala Phe Glu Asp Leu Arg Val
            340                 345                 350

Leu Ser Phe Ile Arg Gly Tyr Pro Ser Ala Ala Phe Glu Asp Leu Arg
        355                 360                 365

Val Leu Ser Phe Ile Arg Gly Tyr Pro Glu Leu Arg Ser Arg Tyr Trp
    370                 375                 380

Ala Ile Arg Thr Arg Ser Gly Pro Glu Leu Arg Ser Arg Tyr Trp Ala
385                 390                 395                 400

Ile Arg Thr Arg Ser Gly Pro Glu Leu Arg Ser Arg Tyr Trp Ala Ile
                405                 410                 415

Arg Thr Arg Ser Gly
            420

<210> SEQ ID NO 87
<211> LENGTH: 1335
<212> TYPE: DNA
<213> ORGANISM: Artificial
<220> FEATURE:
<223> OTHER INFORMATION: Synthetic polynucletide

<400> SEQUENCE: 87
atgagatctc cggcgaaact gctgaaagaa cgtggctttt tggcgcgat tgcgggcttt    60

```
ctggaaggca gcaaagcgta tagcaactgc tatccgtatg atgtgccgga ttacgcgagt      120
ctgggctctc tgctgaccga agtggaaacc tatgtgctgg gctggctgac cggcaaaaac      180
ggcctgtatc cggtgtggac cggcgtgacc cagaacggct tttggcgtgg cgaaaacggc      240
cgtaaaaccc gtagcgcgta tgaacgtatg tgcaacatcc tgaaaggcaa aggcccgaaa      300
tatgtgaaac agaacaccct gaaactggcc accggtgcga gcgcggcgtt tgaggacctg      360
cgtgttctga gctttattcg tggctatggc gaactgcgta gccgttattg ggcgattcgt      420
acccgtagcg gtggtccgcc ggccaaactg ctgaaagaac gcggtttctt cggtgcgatc      480
gccggttttc tggaaggtag caaagcctac tctaattgtt acccgtacga tgttccggat      540
tacgccagcc tgggtagcct gctgaccgaa gttgaaacct acgttctggg ttggctgacc      600
ggtaaaaatg gtctgtaccc ggtttggacc ggtgttaccc agaatggttt ctggcgcggt      660
gaaaatggtc gcaaaacccg cagcgcctac gaacgcatgt gtaatattct gaaaggtaaa      720
ggtccgaaat acgttaaaca gaataccctg aaactggcca ccggcgccag cgccgccttc      780
gaggacctgc gcgttctgag cttcatccgc ggttacggtg aactgcgcag ccgctactgg      840
gccatccgca cccgcagcgg tggtccgccg gcgaaactgc tgaaagaacg cggttttttt      900
ggtgccattg cgggttttct ggaaggtagc aaagcctatt ctaactgcta tccgtacgat      960
gttccggatt atgcgagcct gggtagcctg ctgaccgaag tggaaaccta tgttctgggt     1020
tggctgaccg gcaaaaacgg tctgtatccg gtttggaccg gtgtgaccca gaacggtttt     1080
tggcgcggtg aaaacggccg taaaacccgc agcgcctatg aacgcatgtg caacattctg     1140
aaaggcaaag gtccgaaata cgtgaaacag aacaccctga aactggccac cggcgcgagc     1200
gcggcctttg aggacctgcg cgttctgagc tttattcgcg gctatggtga actgcgcagc     1260
cgctattggg cgattcgtac ccgcagcggc ggctaataac tcgagaagct ttctagacat     1320
atgatgcatg agctc                                                     1335
```

<210> SEQ ID NO 88
<211> LENGTH: 431
<212> TYPE: PRT
<213> ORGANISM: Artificial
<220> FEATURE:
<223> OTHER INFORMATION: Synthetic peptide

<400> SEQUENCE: 88

```
Met Arg Ser Pro Ala Lys Leu Leu Lys Glu Arg Gly Phe Phe Gly Ala
1               5                  10                  15

Ile Ala Gly Phe Leu Glu Gly Ser Lys Ala Tyr Ser Asn Cys Tyr Pro
            20                  25                  30

Tyr Asp Val Pro Asp Tyr Ala Ser Leu Gly Ser Leu Leu Thr Glu Val
        35                  40                  45

Glu Thr Tyr Val Leu Gly Trp Leu Thr Gly Lys Asn Gly Leu Tyr Pro
    50                  55                  60

Val Trp Thr Gly Val Thr Gln Asn Gly Phe Trp Arg Gly Glu Asn Gly
65                  70                  75                  80

Arg Lys Thr Arg Ser Ala Tyr Glu Arg Met Cys Asn Ile Leu Lys Gly
                85                  90                  95

Lys Gly Pro Lys Tyr Val Lys Gln Asn Thr Leu Lys Leu Ala Thr Gly
            100                 105                 110

Ala Ser Ala Ala Phe Glu Asp Leu Arg Val Leu Ser Phe Ile Arg Gly
        115                 120                 125

Tyr Gly Glu Leu Arg Ser Arg Tyr Trp Ala Ile Arg Thr Arg Ser Gly
```

|   |   |   |   |   |   |   |   |   |   |
|---|---|---|---|---|---|---|---|---|---|
|   |   | 130 |   |   | 135 |   |   | 140 |   |

Gly Pro Pro Ala Lys Leu Leu Lys Glu Arg Gly Phe Gly Ala Ile
145                 150                 155                 160

Ala Gly Phe Leu Glu Gly Ser Lys Ala Tyr Ser Asn Cys Tyr Pro Tyr
                165                 170                 175

Asp Val Pro Asp Tyr Ala Ser Leu Gly Ser Leu Leu Thr Glu Val Glu
            180                 185                 190

Thr Tyr Val Leu Gly Trp Leu Thr Gly Lys Asn Gly Leu Tyr Pro Val
        195                 200                 205

Trp Thr Gly Val Thr Gln Asn Gly Phe Trp Arg Gly Glu Asn Gly Arg
    210                 215                 220

Lys Thr Arg Ser Ala Tyr Glu Arg Met Cys Asn Ile Leu Lys Gly Lys
225                 230                 235                 240

Gly Pro Lys Tyr Val Lys Gln Asn Thr Leu Lys Leu Ala Thr Gly Ala
                245                 250                 255

Ser Ala Ala Phe Glu Asp Leu Arg Val Leu Ser Phe Ile Arg Gly Tyr
            260                 265                 270

Gly Glu Leu Arg Ser Arg Tyr Trp Ala Ile Arg Thr Arg Ser Gly Gly
        275                 280                 285

Pro Pro Ala Lys Leu Leu Lys Glu Arg Gly Phe Phe Gly Ala Ile Ala
    290                 295                 300

Gly Phe Leu Glu Gly Ser Lys Ala Tyr Ser Asn Cys Tyr Pro Tyr Asp
305                 310                 315                 320

Val Pro Asp Tyr Ala Ser Leu Gly Ser Leu Leu Thr Glu Val Glu Thr
                325                 330                 335

Tyr Val Leu Gly Trp Leu Thr Gly Lys Asn Gly Leu Tyr Pro Val Trp
            340                 345                 350

Thr Gly Val Thr Gln Asn Gly Phe Trp Arg Gly Glu Asn Gly Arg Lys
        355                 360                 365

Thr Arg Ser Ala Tyr Glu Arg Met Cys Asn Ile Leu Lys Gly Lys Gly
    370                 375                 380

Pro Lys Tyr Val Lys Gln Asn Thr Leu Lys Leu Ala Thr Gly Ala Ser
385                 390                 395                 400

Ala Ala Phe Glu Asp Leu Arg Val Leu Ser Phe Ile Arg Gly Tyr Gly
                405                 410                 415

Glu Leu Arg Ser Arg Tyr Trp Ala Ile Arg Thr Arg Ser Gly Gly
            420                 425                 430

<210> SEQ ID NO 89
<211> LENGTH: 13
<212> TYPE: PRT
<213> ORGANISM: Artificial
<220> FEATURE:
<223> OTHER INFORMATION: Synthetic peptide

<400> SEQUENCE: 89

Pro Arg Tyr Val Lys Gln Asn Thr Leu Lys Leu Ala Thr
1               5                   10

MULTIMERIC MULTIEPITOPE POLYPEPTIDES IN IMPROVED SEASONAL AND PANDEMIC INFLUENZA VACCINES

FIELD OF THE INVENTION

The present invention relates to a method for improving and enhancing the protective effect of conventional seasonal or pandemic influenza vaccines by administering a multimeric multi-epitope peptide-based vaccine. The present invention further provides pharmaceutical compositions comprising a multimeric multi-epitope polypeptide and another influenza vaccine and their use for protecting subjects against influenza.

BACKGROUND OF THE INVENTION

Influenza is a highly infectious disease caused by rapidly mutating influenza viruses. It is easily transmitted and spreads around the world in seasonal epidemics, affecting 10-20% of the total population annually. According to the World Health Organization (WHO), 250,000-500,000 people die annually of seasonal influenza-related causes during epidemic outbreaks. In the USA alone more than 200,000 people are hospitalized with seasonal influenza in a typical year. Influenza infection may be mild, moderate or severe, ranging from asymptomatic through mild upper respiratory infection and tracheobronchitis to a severe, occasionally lethal, viral pneumonia. The infection is associated with pulmonary and cardiovascular complications leading to high morbidity and mortality rates, affecting mainly at-risk populations such as toddlers, elderly and individuals with chronic medical conditions.

Influenza viruses have two important immunological characteristics that present a challenge to vaccine preparation. The first concerns genetic changes that occur in the surface glycoproteins every year, referred to as "antigenic drift". This antigenic change produces viruses that elude resistance elicited by existing vaccines. The second characteristic of great public health concern is that influenza viruses, in particular influenza A virus can exchange genetic material and merge. This process, known as "antigenic shift", results in new strains different from both parent viruses, which can be lethal pandemic strains.

Of the three types of influenza viruses, Influenza A and Influenza B are responsible for approximately 80% and 20% of influenza disease in humans, respectively, while influenza C viruses do not infect humans. Influenza A viruses are characterized by many sub-strains and by species specificity and are considered to be the major cause of widespread seasonal epidemics and of pandemics, due to the frequent antigenic drifts and shifts of the Hemagglutinin (HA) and Neuraminidase (NA) surface proteins. Following antigenic changes, infection via virus strains which are unrecognized by the immune system may result in a reduced immune response by the infected individual, where more significant changes will yield less effective stimulation of the body's immune defenses. Antigenic drifts or shifts can trigger respective influenza epidemics or pandemics, as experienced with the recent Avian and Swine Flu pandemic strains.

Immunization towards influenza virus is limited by the antigenic variation of the virus. The influenza vaccines currently available are the following: whole virus vaccines—inactivated or live-attenuated virus; split virus vaccines (virus fragments); subunit vaccines or purified antigens (in which the surface proteins Hemagglutinin (HA) and Neuraminidase (NA) are purified from other virus components); and virosomal vaccines: synthetic virus-like particles with embedded HA and NA virus surface proteins.

To date, commercially available influenza vaccines contain influenza A and B antigens that are annually selected according to predictions of the strains to be most prevalent during the peak influenza season. However, due to the mismatch between the strains included in the vaccine and those actually circulating, these strain-specific vaccines often have relatively poor clinical efficacy. In addition, such immunization methods require preparation of new vaccine formulations on an annual basis. Thus, a vaccine recognizing multiple virus strains would be more cost effective and would further increase patient compliance and enhance global health prospects.

PCT International Publication WO 2009/016639 to some of the inventors of the present invention discloses influenza multi-epitope polypeptides and vaccines comprising a plurality of influenza virus peptide epitopes wherein each epitope is present at least twice in a single polypeptide.

The Multimeric-001 (M-001) vaccine consists of nine conserved linear epitopes arranged as three repetitions of each and prepared as a single, recombinant protein expressed in *E. coli*. These epitopes are common to the vast majority of influenza virus strains, regardless of their antigenic drifts and shifts. Consequently, M-001 is expected to provide immunity-based protection against future virus strains as well. The chosen epitopes activate both the humoral and cellular arms of the immune system, creating maximal efficacy in antigen-stimulated resistance to infection (Adar Y et al. Vaccine, 2009; 27, 2099-2107).

Previous experimental studies performed in young and aged mice and rats, indicate that administration of the epitopes included in the Multimeric-001 vaccine leads to efficient cross-strain protection against influenza. Both humoral and cellular immune arms were activated in mice that received three vaccinations at three week intervals. Antibodies raised against M-001 demonstrated cross-strain influenza recognition, despite variations in the outer proteins of each strain. Moreover, lysis of MDCK cells infected with the influenza virus was recorded upon incubation with anti-M-001 antibodies, suggesting a mechanism of action for the humoral response to the vaccine.

The significant results obtained with various animal models and the safety parameters observed in the repeated toxicology study have paved the way toward, and provided the foundation for, clinical trials in humans.

The M-001 vaccine has been administered in both adjuvanted and non-adjuvanted formulations. A Phase I/II clinical trial assessing the safety and efficacy of M-001 in young, healthy volunteers was recently completed. Doses of 125-500 µg adjuvanted or non-adjuvanted vaccine proved safe and well tolerated. In addition, the adjuvanted 500 µg M-001 dose induced most significant immune responses, when compared to the other treatment groups.

Potential Multimeric-001 vaccine-related toxicity was evaluated in toxicology studies. Both M-001 vaccine formulations (adjuvanted and non-adjuvanted) repeatedly IM administered at the maximal human dose, proved to be safe.

Thus there is an unmet need for improvement of the protective effect of seasonal vaccines against influenza by an influenza peptide epitope-based vaccine which can induce humoral and cellular responses that are long-lasting with broad specificity.

SUMMARY OF THE INVENTION

The present invention provides a method of improving the protective effect of an influenza vaccine by administering to a subject in need thereof, prior to or together with the influenza vaccine, at least one multimeric influenza polypeptide comprising multiple copies of plurality of influenza virus peptide epitopes. As demonstrated herein in animal and human studies, the multimeric influenza polypeptides are particularly effective as enhancers of seasonal and pandemic vaccines against influenza that improve anti-influenza immune responses e.g. by increasing sero-protection as measured by Hemagglutination Inhibition (HAI). Significantly, the improved HAI responses were directed not only against influenza strains whose HA were included in a concomitantly or co-administered seasonal influenza vaccine, but also against strains whose HA were not included in such vaccines. These results are particularly surprising since the multimeric influenza polypeptide does not contain any peptide epitopes which are from the HA hypervariable region and are responsible for or active in HAI responses from any influenza strain.

The present invention further provides pharmaceutical compositions comprising a combination composition comprising at least one synthetic or recombinant multimeric influenza polypeptide and at least one conventional seasonal or pandemic influenza composition. A conventional seasonal vaccine (TIV) typically contains three inactivated or live attenuated influenza virus strains selected each year by the WHO to provide protection against the strains that are expected to infect in the coming season. A pandemic vaccine typically includes one influenza virus strain specific to the relevant strain causing the pandemic.

A multimeric polypeptide according to the present invention is a synthetic or recombinant polypeptide comprising a plurality of influenza virus peptide epitopes each epitope is present at least twice in a single polypeptide. Within the context of this invention, a "multimeric" polypeptide is a polypeptide that contains a plurality of repeats (at least two, typically at least three or more), not necessarily adjacent, of an amino acid stretch of the polypeptide. The term "multimeric multi-epitope" therefore relates to a polypeptide containing a plurality of repeats of a plurality of epitopes. Multimeric multi-epitope polypeptide can be produced recombinantly, as an isolated polypeptide or as a fusion protein, or synthetically by linking a plurality of synthetic peptides, or can be mixed or formulated with an external adjuvant.

Multimeric polypeptides of the invention contain a combination of influenza virus B-cell epitopes, T-helper epitopes, and cytotoxic lymphocyte (CTL) epitopes. The epitopes are preferably selected from conserved (non-hypervariable) regions of hemagglutinin protein (HA) peptides, matrix protein (M1 and/or M2) peptides, and nucleoprotein (NP) peptides. The epitopes have a demonstrable cross-reaction activity against several human influenza subtypes and are chosen for their improved ability to induce a cellular and humoral immune responses.

It was surprisingly found in clinical trials, that vaccination of elderly subjects with multimeric polypeptides prior to or together with vaccination with commercial seasonal inactivated trivalent (TIV) influenza vaccine result in increased sero-protection, seroconversion and/or mean geometric increase (GMT), measured by Hemagglutination Inhibition (HAI) responses, to the viruses included in the vaccine. These increased responses were directed not only against virus serotypes included in the seasonal vaccine, but also against virus serotypes which were not included in the seasonal vaccine. Hemagglutination responses correlate positively with protection against influenza and is used by the regulatory authorities to measure the effectiveness of influenza vaccines.

The present invention provides, according to one aspect, a method for improving the protective effect of seasonal or pandemic influenza vaccine by vaccination of a subject in need thereof, prior to, or together with administration of the seasonal or pandemic vaccine, an effective amount of a synthetic or recombinant influenza multi-epitope polypeptide.

An effective amount of a synthetic or recombinant influenza multi-epitope polypeptide is an amount sufficient to elicit specific humoral and cellular immune responses against influenza.

According to some embodiments, the improvement in the protective effect is demonstrated as increased HAI responses. According to some embodiments the increased HAI responses are against virus serotypes included in such administered seasonal or pandemic vaccines. According to other embodiments the increased sero-protection is directed against virus serotypes which are not included in such administered seasonal or pandemic vaccines. According to some embodiments the increased HAI response is demonstrated in at least one parameter selected from the group consisting of: seroconversion, seroprotection and GMT. According to one embodiment, the multimeric polypeptide is administered by vaccination, prior to administration of the seasonal or pandemic influenza vaccine which, according to this embodiment of the present invention, denotes that at least 24 hours transpire between vaccination with the multimeric polypeptide and administration of the seasonal or pandemic influenza vaccine. According to some embodiments, the multimeric polypeptide is administered by vaccination at least one week before administering the seasonal or pandemic vaccine. According to other embodiments the multimeric polypeptide is administered 1-5 weeks prior to administering seasonal or pandemic vaccines. According to yet other embodiments the multimeric vaccine is administered 10-25 days before administering the seasonal or pandemic vaccine. Each possibility represents a separate embodiment of the present invention.

According to other embodiments the multimeric polypeptide is co-administered with the seasonal or pandemic influenza vaccine. Co-administered according to the present invention encompass either that both the multimeric polypeptide and the seasonal or pandemic vaccine are included in one combined composition, or that they are administered to the patient within about 24 hours in two separate vaccinations.

According to some embodiments, the dose of a seasonal or pandemic influenza vaccine required to elicit a protective response against influenza in a subject is significantly decreased following prior or co-administration of a multimeric polypeptide according to the invention to the immunized subject. A significantly decreased amount refers to an amount of maximum 50% of the routine prescribed dose of the seasonal or pandemic vaccine. According to some embodiments, the decreased amount of the seasonal or pandemic vaccine is 15-50% of the regular prescribed dose.

According to some embodiments the route of administration of the multimeric vaccine, the seasonal or pandemic vaccine or the combined composition is selected from intramuscular, intranasal, oral, intraperitoneal, subcutaneous, topical, intradermal, and transdermal delivery. According to preferred embodiments the multimeric vaccine, the seasonal or pandemic vaccine or the combined composition is administered intranasally, intramuscularly or intradermally.

According to some embodiments of the present invention the subject immunized by the multimeric vaccine is equal to or older than 55 years of age.

The synthetic or recombinant influenza multi-epitope polypeptide used according to the present invention is selected from the group consisting of:
i. $B(X_1ZX_2Z \ldots X_m)_nB$; and
ii. $B(X_1)_nZ(X_2)_nZ \ldots (X_m)_nB$;

wherein B denotes a sequence of 0-4 amino acid residues; n is at each occurrence independently an integer of 2-50; m is an integer of 3-50; each of $X_1, X_2 \ldots X_m$ is an influenza peptide epitope consisting of 4-24 amino acid residues; Z at each occurrence is a bond or a spacer of 1-4 amino acid residues; and wherein the maximal number of amino acid residues in the polypeptide is about 1000. Each possibility represents a separate embodiment of the present invention.

According to some embodiments n is at each occurrence independently an integer of 2-50; m is an integer of 3-15; each of $X_1$-$X_m$ is an influenza peptide epitope selected from the group consisting of a B-cell type epitope, a T-helper (Th) type epitope, and a cytotoxic lymphocyte (CTL) type epitope, consisting of 4-24 amino acid residues; and the maximal number of amino acid residues in the polypeptide is about 600. Each possibility represents a separate embodiment of the present invention.

According to other embodiments the influenza peptide epitopes of the multimeric polypeptide are selected from the group consisting of a Hemagglutinin (HA) peptide, an M1 peptide, an M2 peptide, and a nucleoprotein (NP) peptide. Each possibility represents a separate embodiment of the present invention.

According to some specific embodiments m is 9 and n is an integer of 3-5. Each possibility represents a separate embodiment of the present invention.

According to other embodiments the influenza peptide epitopes within the multimeric polypeptide used according to the present invention are selected from the group consisting of SEQ ID NO:1 to SEQ ID NO:82. Each possibility represents a separate embodiment of the present invention.

According to some specific embodiments the influenza peptide epitopes are selected from epitopes E1-E9 according to table 1:

of: SEQ ID NO:84, SEQ ID NO:86, and SEQ ID NO:88. Each possibility represents a separate embodiment of the present invention.

According to yet other embodiments the multimeric polypeptide sequence is encoded by a polynucleotide sequence selected from the group consisting of: SEQ ID NO:83, SEQ ID NO:85, and SEQ ID NO:87. Each possibility represents a separate embodiment of the present invention.

According to some preferred embodiments the multimeric polypeptide comprises three repeats of nine different influenza virus peptide epitopes arranged in the following block copolymer structure [E1E1E1-E2E2E2-E3E3E3-E4E4E4-E5E5E5-E6E6E6-E7E7E7-E8E8E8-E9E9E9], wherein E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51), E6 is NP 206-229 (SEQ ID NO:64), E7 is HA 307-319 (SEQ ID NO:59 or 89), E8 is NP 335-350 (SEQ ID NO:69), and E9 is NP 380-393 (SEQ ID NO:70).

According to other embodiments the multimeric polypeptide comprises nine different influenza virus peptide epitopes arranged in the following alternating sequential polymeric structure [E1E2E3E4E5E6E7E8E9]$_n$, wherein n is 3 or 5; E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51), E6 is NP 206-229 (SEQ ID NO:64), E7 is HA 307-319 (SEQ ID NO:59 or 89), E8 is NP 335-350 (SEQ ID NO:69), and E9 is NP 380-393 (SEQ ID NO:70).

According to yet other embodiments the multimeric polypeptide comprises six repeats of five different B-cell type influenza virus peptide epitopes arranged in the following alternating sequential polymeric structure [E1E2E3E4E5]$_6$, wherein E1 is HA 354-372 (SEQ ID NO:82), E2 is HA

TABLE 1 influenza peptide epitopes E1 to E9

| Epitope | Epitope Type | Protein residues | Amino Acid Sequence | SEQ ID NO: |
|---|---|---|---|---|
| E1 | B cell | HA 354-372 | PAKLLKERGFFGAIAGFLE | 82 |
| E2 | B cell | HA 91-108 | SKAYSNCYPYDVPDYASL | 48 |
| E3 | B cell & CTL | M1 2-12 | SLLTEVETWL | 25 |
| E4 | B cell | HA 150-159 | WLTGKNGLYP | 52 |
| E5 | B cell | HA 143-149 | WTGVTQN | 51 |
| E6 | T helper | NP 206-229 | FWRGENGRKTRSAYERMCNILKGK | 64 |
| E7 | T helper | HA 307-319 | PK/RYVKQNTLKLAT | 59, 89 |
| E8 | CTL | NP 335-350 | SAAFEDLRVLSFIRGY | 69 |
| E9 | CTL | NP 380-393 | ELRSRYWAIRTRSG | 70 |

According to more specific embodiments the influenza peptide epitopes included in a multimeric polypeptide used according to the present invention consist of: HA 354-372 (E1, SEQ ID NO: 82), HA 91-108 (E2, SEQ ID NO: 48), M1 2-12 (E3, SEQ ID NO: 25), HA 150-159 (E4, SEQ ID NO: 52), HA 143-149 (E5, SEQ ID NO: 51), NP 206-229 (E6, SEQ ID NO: 64), HA 307-319 (E7, SEQ ID NO: 59 or 89), NP 335-350 (E8, SEQ ID NO: 69), and NP 380-393 (E9, SEQ ID NO: 70).

According to yet other embodiments the multimeric polypeptide sequence is selected from the group consisting 91-108 (SEQ ID NO:48), E3 is M1 2-12 (SEQ ID NO:25), E4 is HA 150-159 (SEQ ID NO:52), E5 is HA 143-149 (SEQ ID NO:51).

According to other embodiments the multimeric polypeptide comprises six repeats of four different T-cell type influenza virus peptide epitopes arranged in the following alternating sequential polymeric structure [E7E8E9E6]$_6$, wherein E6 is NP 206-229 (SEQ ID NO:64), E7 is HA 307-319 (SEQ ID NO:59 or 89), E8 is NP 335-350 (SEQ ID NO:69), and E9 is NP 380-393 (SEQ ID NO:70).

According to additional embodiments the multimeric polypeptide comprises six repeats of nine different influenza virus peptide epitopes arranged in the following block copolymer structure [E2E2E2E2E2E2-E1E1E1E1E1E1-E3E3E3E3E3E3-E4E4E4E4E4E4-E5E5E5E5E5E5-E6E6EE6E6E6-E7E7E7E7E7E7-E8E8E8E8E8E8-E9E9E9E9E9E9], wherein E1 is HA 354-372 (SEQ ID NO:82), E2 is HA 91-108 (SEQ ID NO:48), E3 is M1 2-12 (SEQ ID NO:25), E4 is HA 150-159 (SEQ ID NO:52), E5 is HA 143-149 (SEQ ID NO:51), E6 is NP 206-229 (SEQ ID NO:64), E7 is HA 307-319 (SEQ ID NO:59 or 89), E8 is NP 335-350 (SEQ ID NO:69), and E9 is NP 380-393 (SEQ ID NO:70).

In various embodiments the multimeric polypeptide comprises at least two repeats of each epitope, typically at least three repeats of each epitope, alternatively at least four repeats, alternatively at least five repeats, alternatively at least six repeats of each epitope, maximum at least 50 repeats of each epitope. To improve the exposure of the epitopes to the immune system, the epitopes are preferably separated by a spacer, which according to certain embodiments consists of a single amino acid and according to other embodiments comprises at least one amino acid or is a peptide. Preferably, the spacer consists of 1-4 neutral amino acid residues. Each possibility represents a separate embodiment of the present invention.

In some embodiments of this aspect of the present invention, the multimeric multiepitope polypeptide comprises at least two influenza peptide epitopes wherein at least one is selected from the group consisting of B-cell type epitopes, T-helper (Th) type epitopes, and cytotoxic lymphocyte (CTL) type epitopes. In some embodiments, the influenza peptide epitopes are selected from the group consisting of hemagglutinin (HA) peptide epitopes, matrix protein (M1 and/or M2) peptide epitopes, and nucleoprotein (NP) peptide epitopes. In certain preferred embodiments the peptide epitopes are selected from the group consisting of epitopes E1 to E9 according to Table 1. Each possibility represents a separate embodiment of the present invention.

According to some embodiments peptide epitopes within a multimeric polypeptide are linked by a spacer selected from the group consisting of: a bond, an amino acid, and a peptide comprising at least two amino acids.

According to some embodiments at least one amino acid of the spacer induces a specific conformation on a segment of the polypeptide (e.g. a proline residue).

According to yet other embodiments the spacer comprises a cleavable sequence. According to one embodiment the cleavable spacer is cleaved by intracellular enzymes. According to a more specific embodiment the cleavable spacer comprises a protease specific cleavable sequence.

According to some embodiments the multimeric polypeptide are preferably not conjugated to and are devoid of a carrier fusion protein. In other embodiments the polypeptides of the present invention may further comprise a carrier sequence, namely the peptide epitopes are inserted within a sequence of a carrier polypeptide or are coupled to a carrier sequence. According to some embodiments, the multimeric polypeptides are produced as a recombinant fusion protein comprising a carrier sequence. In some specific embodiments the multi-epitope polypeptide is inserted within the sequence of the carrier, thereby forming a recombinant carrier fusion protein containing the multimeric multiepitope polypeptide. In other embodiments, the polypeptide is fused to an amino terminal or a carboxy terminal portion of the carrier protein.

According to yet another aspect, the present invention provides a vaccine composition for immunization of a subject against influenza comprising at least one synthetic or recombinant influenza multi-epitope polypeptide comprising multiple copies of a plurality of influenza virus peptide epitopes and at least one seasonal or pandemic preparation against influenza.

Any vaccine against influenza can be used in conjunction with the multimeric polypeptides in methods and compositions according to the present invention. The term "vaccines against influenza" includes but is not limited to, partially or highly purified or recombinant influenza proteins, inactivated viruses or "split product" inactivated influenza vaccine products, live attenuated viruses, or particles or carriers displaying influenza epitopes, including but not limited to virus like particles (VLP) and liposomes. Influenza vaccine to be used in conjunction with the multimeric polypeptides can be seasonal, pandemic or universal vaccines.

A non-limitative list of specific seasonal vaccines that can be used according to the present invention includes: Vaxigrip™, Aggripal™, Fluvirin™, Fluad™, Mutagrip™ Fluzone™, Influvac™, Fluarix™, Flulaval™, FluMist™, Afluria™, Agriflu™. According to other embodiments the pandemic vaccine is against human, swine or avian influenza strains. A non-limitative list of specific pandemic vaccines that can be used according to the present invention includes: Panenza™, Pandemrix, Humenza, Focetria, Celvapan, Celtura, and Flumist.

In some embodiments, the vaccine comprises at least two influenza peptide epitopes wherein at least one epitope is selected from the group consisting of B-cell type epitopes, T-helper (Th) type epitopes, and CTL type epitopes. In some embodiments, the influenza peptide epitopes are selected from the group consisting of hemagglutinin (HA) peptide epitopes, M1 peptide epitopes, M2 peptide epitopes, and NP peptide epitopes. In preferred embodiments the peptide epitopes are selected from the group consisting of the epitopes E1 to E9 in Table 1 above.

In one embodiment the vaccine comprises three repeats of the nine epitopes arranged according to the block copolymer structure $[E1]_3$-$[E2]_3$-$[E3]_3$-$[E4]_3$-$[E5]_3$-$[E6]_3$-$[E7]_3$-$[E8]_3$-$[E9]_3$. In another embodiment the vaccine comprises five repeats of the nine epitopes arranged according to the alternating sequential polymeric structure $[E1E2E3E4E5E6E7E8E9]_5$. In yet another embodiment the vaccine comprises three repeats of the nine epitopes E1-E9, arranged according to the alternating sequential polymeric structure $[E1E2E3E4E5E6E7E8E9]_3$. In yet another embodiment the vaccine comprises six repeats of the nine epitopes arranged according to the block copolymer structure $[E1]_6$-$[E2]_6$-$[E3]_6$-$[E4]_6$-$[E5]_6$-$[E6]_6$-$[E7]_6$-$[E8]_6$-$[E9]_6$.

According to some embodiments the vaccine compositions according to the present invention do not contain an adjuvant. According to other embodiments the vaccine further comprises an adjuvant.

Pharmaceutically acceptable adjuvants include, but are not limited to water in oil emulsion, lipid emulsion, or submicron oil in water emulsion and liposomes. According to specific embodiments the adjuvant is selected from the group consisting of: Montanide™ alum, muramyl dipeptide, Gelvac®, chitin microparticles, chitosan, cholera toxin subunit B, Intralipid®, Lipofundin,® or bacterial lipids, lipoproteins, and/or membrane proteins. According to a current preferred embodiment the adjuvant is Montanide™.

In some embodiments the vaccine is formulated for intramuscular, intranasal, oral, intraperitoneal, subcutaneous, topical, intradermal and transdermal delivery. In some embodiments the vaccine is administered intranasally. In other embodiments the vaccine is administered intramuscularly. In yet other embodiments the vaccine is administered intradermally.

The present invention provides according to a further aspect a method for inducing an immune response and conferring protection against influenza in a subject, comprising administering to the subject a vaccine composition comprising at least one synthetic or recombinant influenza multiepitope polypeptide comprising multiple copies of a plurality of influenza virus peptide epitopes and at least one seasonal or pandemic composition against influenza.

The route of administration of the vaccine is selected from intramuscular, intranasal, oral, intraperitoneal, subcutaneous, topical, intradermal, and transdermal delivery. According to preferred embodiments the vaccine is administered intranasally, intramuscularly or intradermally.

Use of a polypeptide according to the invention for preparation of a vaccine composition for immunization against influenza is also within the scope of the present invention, as well as use of an isolated polynucleotide according to the invention for production of a polynucleotide.

The multimeric polypeptides disclosed in the present invention can be produced as a recombinant protein, a fusion protein, and by chemical synthesis. Accordingly, another aspect of the present invention provides a recombinant protein comprising a multimeric multiepitope polypeptide comprising a plurality of influenza virus peptide epitopes.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
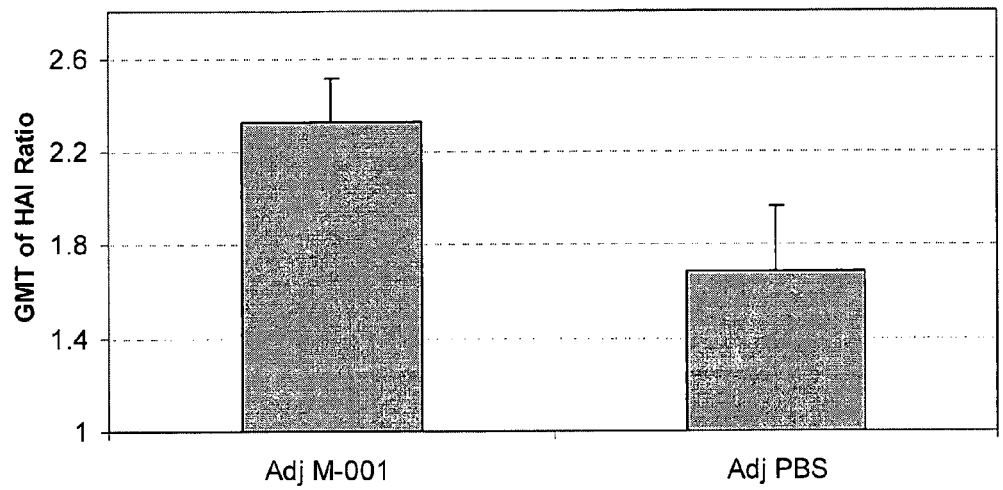
FIG. 1: Improved Homologous H1N1 HAI response to lower-dose TIV (Vaxigrip) after administration of M-001 to mice. Average ratio of HAI 14 days after immunization with 1.5% of standard Vaxigrip dose compared to HAI tit heterologous HAI titres recognizing virus strains not included in the seasonal TIV administered. HAI titres recognizing A/H1N1 (A), A/H3N2 (B) and influenza B (C) virus strains that were not included in the seasonal TIV administered were improved in subjects co-administered with both seasonal TIV plus adjuvanted M-001 for several different strains tested. Percent of seroconverted subjects was calculated as a) the number of subjects per cohort expressing a mean fold increase in anti-HA antibody levels ≥4-fold compared to levels in sera collected on day 0, with b) HAI titers ≥40 post-immunization.
Figure 2:
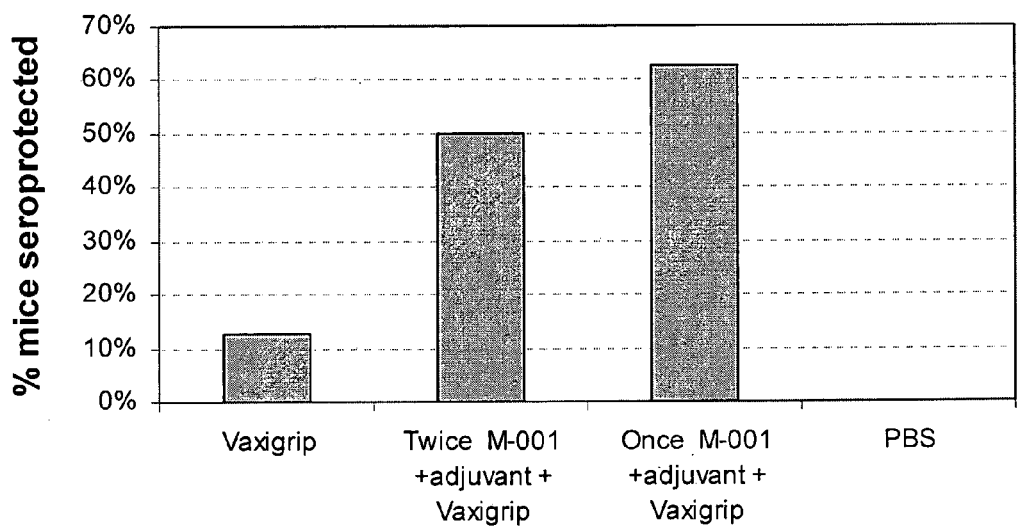

Universal, strain-independent multimeric multiepitope polypeptides according to the present invention are used as super-seasonal influenza vaccines for immunizing subjects, prior to or together with immunizing the subject with a seasonal or pandemic influenza vaccine. This novel vaccination regimes and compositions improve significantly the protective effect of said seasonal or pandemic vaccine.

It is shown herein in both human and animal models, that the potential of M-001 to act as a primer for a boost from the trivalent inactivated seasonal vaccine (TIV), either by consecutive immunizations (immunizing once or twice with M-001 and then, two or three weeks later, with the TIV) or by successive administrations (M-001 and TIV on the same day). It was found that the prime-boost combination vaccines showed enhanced efficacy over the use of the TIV alone. The efficacy was measured by seroconversion to HA antibodies in an HAI assay which is the assessment accepted by the regulatory authorities and its results correlate with protection against influenza infection. The improved efficacy was shown both towards virus strains contained in the seasonal vaccine as well as toward other strains not included in this specific seasonal vaccine.

In a human trial, sixty subjects (55-75 years old) were immunized twice with the Multimeric vaccine M-001 and three weeks later boosted with a whole dose of the seasonal 2009/2010 vaccine Vaxigrip®. The humoral and cellular immunity found on day 42 (after 2 IM administrations of the M-001) and on day 63 (after boosting with a whole dose of Vaxigrip®) indicates improved efficacy, in terms of seroconversion measured by HAI, of subjects primed with M-001 as compared to subjects who were immunized with the seasonal vaccine only. Unexpectedly, the efficacy of the seasonal vaccine (measured by HAI seroconversion) to other viruses that are not included in the vaccine, was enhanced in 10 of 13 viruses tested. This enhancement was demonstrated in strains H1N1, H3N2 and in B strains from both Victoria and Yamagata lineages, showing the potential of the prime-boost combination vaccines to induce immune responses against new strains.

Universal multimeric multiepitope vaccines may be also used according to the present invention for enhancement of the protective effect of any other vaccine against influenza, including to other universal stain-independent influenza vaccines, by administering the multimeric vaccine prior to or together with the other influenza vaccine.

Although universal multimeric vaccines are capable of eliciting a protective immune response against influenza without influencing HAI seroconversion, their administration prior to or together with seasonal or pandemic vaccines unexpectedly result in significant increase in HAI seroconversion to both strains included in the seasonal or pandemic vaccines and even to several other strains not included in these vaccines. Without wishing to be bound to any theory it is suspected that as the multimeric polypeptides include conserved and common T helper epitopes, shared by many strains of influenza virus it enhances the overall immunity to influenza.

The cross protective potential of the M-001 vaccine is also shown by the prime-boost approach. In patients primed with different formulations of M-001, improvement of the seroconversion, seroprotection and GMT parameters towards viruses within the TIV was observed. Interestingly, in 10 out of 13 viruses representing H1N1, H3N2 and influenza B from both Victoria and Yamagata lineages, there was an improved response as measured by the percentage of participants that were seroconverted.

The multimeric polypeptides of the present invention contain conserved B- and T-cell epitopes from various influenza proteins, and induce humoral and cellular immune responses that are specific to a diversity of influenza viruses and hence, they are not and can not be considered as an adjuvant that activates non specific immune responses.

When administered alone, in pre clinical studies, the multimeric polypeptide induced lymphocytes proliferation that was associated with Th1 cytokines secretion. The antibody response to the Multimeric was also influenza specific as shown in ELISA assays and in a complement lysis of infected cells that were incubated in-vitro with the anti-multimeric antibodies. Furthermore, in human, following two IM administrations of the multimeric polypeptide resulted in the same findings, i.e. lymphocytes proliferation associated with IFN-gamma and IL-2 secretion as well as functional antibodies to various strains of influenza. Control groups, immunized with adjuvant alone, both in pre clinical and clinical studies did not induce any influenza specific immune responses. Together with these specific anti influenza properties of the Multimeric polypeptide, elevated HAI responses are demonstrated when the Multimeric polypeptide is administered with TIV in comparison to TIV administration alone, as detailed in the present invention.

A multimeric polypeptide used in vaccines and methods according to the present invention comprises at least two repeats of each epitope. Preferably a multimeric polypeptide according to the present invention comprises at least three repeats of each epitope.

The present invention provides vaccines comprising a seasonal or pandemic vaccine and at least one multimeric multiepitope polypeptide, comprising a plurality of influenza virus peptide epitopes. Methods of use of such vaccines are also provided. Various exemplary embodiments are provided, for multimeric vaccines comprising epitopes selected from Table 1, wherein the number of repeats for each epitope is the same or different and wherein the polypeptide can be arranged in an alternating sequential polymeric structure or a block copolymer structure. The term "alternating sequential polymeric" structure means that a single copy of all the epitopes contained in the polypeptide are arranged sequentially and this arrangement is repeated sequentially a number of times equal to the number of repeats. For example, if the multimeric multiepitope polypeptide comprises four repeats of three epitopes $X_1$, $X_2$ and $X_3$ in an alternating sequential structure, the polypeptide has the following polymeric structure: $X_1X_2X_3$-$X_1X_2X_3$-$X_1X_2X_3$-$X_1X_2X_3$, also written $[X_1X_2X_3]_4$. The term "block copolymer" structure means that all the copies of a single epitope contained in the polypeptide are arranged adjacently. For example, a similar multimeric multiepitope polypeptide comprising four repeats of three epitopes $X_1$, $X_2$ and $X_3$ in a block copolymer structure has the following polymeric structure: $X_1X_1X_1X_1$-$X_2X_2X_2X_2$-$X_3X_3X_3X_3$, also written $[A]_4$-$[B]_4$-$[C]_4$.

DEFINITIONS

For convenience, certain terms employed in the specification, examples and claims are described herein.

A conventional seasonal vaccine typically contains three inactivated or live attenuated influenza virus strains and is therefore denoted also TIV (trivalent influenza vaccine). The three strains are selected each year by the WHO to provide protection against the strains that are expected to infect in the coming season.

A pandemic vaccine typically includes one influenza virus strain specific to the relevant strain causing the pandemic. For example, The A/H1N1 strain used for swine flu pandemic during 2009/2010 season, was then included in the seasonal TIV formulation in the 2010/2011 season.

Seroconversion and seroprotection: seroconversion to HA antibodies is measured in an HAI assay which is the test accepted by the regulatory authorities to correlate with protection against influenza infection. Serial two-fold dilutions of serum collected from vaccinated subjects are incubated with the test viruses to determine the dilution at which inhibition of unbound erythrocyte agglutination no longer occurs. The reciprocal of the dilution at which this occurs is then defined as the HAI titer. Subjects are considered seroconverted toward a specific influenza virus when the fold increase in HAI titers is ≥4-fold from that of baseline titers as measured in sera collected on day 0 of the study and diluted 1:10. An adult subject is considered seroprotected when expressing HAI titers of ≥40 in the end-pint measurement. Criteria for assessment of vaccines (CHMP) for adults (18-60 years old) include 40% seroconversion and 70% seroprotection, mean geometric increase (GMT) of HAI titers, should be >2.5. For subjects aged over 60, at least one of the following criteria should meet the indication: 30% seroconversion, 60% seroprotection, or GMT >2.0 (Committee for Proprietary Medicinal Products (CPMP), Note for Guidance on Harmonisation of Requirements for Influenza Vaccines (CPMP/BWP/214/96) http://www.ema.europa.eu/docs/en_GB/document_library/Scientific_guideline/2009/09/WC500003945.pdf).

The term "immunogenicity" or "immunogenic" relates to the ability of a substance to stimulate or elicit an immune response. Immunogenicity is measured, for example, by determining the presence of antibodies specific for the substance. The presence of antibodies is detected by methods known in the art, for example using an ELISA or HAI assay.

The term "antigen presentation" means the expression of antigen on the surface of a cell in association with major histocompatibility complex class I or class II molecules (MHC-I or MHC-II) of animals or with the HLA-I and HLA-II of humans.

Influenza epitopes can be classified as B-cell type, T-cell type or both B cell and T cell type, depending on the type of immune response they elicit. The definition of B cell or T cell peptide epitope is not unequivocal; for example, a peptide epitope can induce antibody production but at the same time that epitope can possess a sequence that enables binding to the human HLA molecule, rendering it accessible to CTLs, hence a dual B cell and T cell classification for that particular epitope. "CTL", "killer T cells" or "cytotoxic T cells" is a group of differentiated T cells that recognize and lyse target cells bearing a specific foreign antigen that function in defense against viral infection and cancer cells. "T helper cell" or "Th" is any of the T cells that when stimulated by a specific antigen release cytokines that promote the activation and function of B cells and killer T cells.

"Amino acid sequence", as used herein, refers to an oligopeptide, peptide, polypeptide, or protein sequence, and fragment thereof, and to naturally occurring or synthetic molecules.

In the specification and in the claims the term "spacer" denotes any chemical compound, which may be present in the polypeptide sequence, at one of the terminals or between two epitopes. Preferably, the spacer consists of 1-4 amino acid residues. The spacer may comprise a sequence that can be cleaved by enzymatic means, or may decompose spontaneously. The spacer may enforce or induce beneficial conformation to the polypeptide. The spacer may optionally comprise a protease specific cleavable sequence.

Peptide Epitopes Useful in Preparing a Multimeric Vaccine

According to preferred embodiments of the present invention, peptide epitopes included in the multimeric polypeptides, are derived from influenza proteins selected from the group consisting of HA, M1, M2, and NP. The epitopes may also be selected according to their type: B-cell type, Th type, and CTL type.

It is to be noted that peptide epitopes listed herein are provided as for exemplary purposes only. The influenza virus proteins vary between isolates, thereby providing multiple variant sequences for each influenza protein. Accordingly, the present invention encompasses peptide epitopes having one or more amino acid substitutions, additions or deletions.

Chimeric or Recombinant Molecules

A "chimeric protein", "chimeric polypeptide" or "recombinant protein" are used interchangeably and refer to an influenza multimeric polypeptide operatively linked to a polypeptide other than the polypeptide from which the peptide epitope was derived. The multimeric multiepitope polypeptides of the present invention can be prepared by expression in an expression vector per se or as a chimeric protein. The methods to produce a chimeric or recombinant protein comprising one or more influenza peptide epitopes are known to those with skill in the art. A nucleic acid sequence encoding one or more influenza peptide epitopes can be inserted into an expression vector for preparation of a polynucleotide construct for propagation and expression in host cells. A nucleic acid construct encoding a polypeptide comprising multiple repeats of several epitopes, such as a multimeric multiepitope polypeptide, can be prepared by ligation of smaller polynucleotide constructs bearing appropriated restriction sites at their 3' and 5' ends.

In a non-limiting example, the chimeric polypeptide of the present invention includes chimeras of an influenza peptide epitope with one of the following, polypeptides: Cholera toxin, Tetanus toxin, Ovalbumin, Tuberculosis heat shock protein, Diphtheria Toxoid, Protein G from respiratory syncytial virus, Outer Membrane Protein from *Neisseria meningitides*, nucleoprotein of vesicular stomatitis virus, glycoprotein of vesicular stomatitis virus, *Plasmodium falciparum* Antigen Glutamate-Rich Protein, Merozoite Surface Protein 3 or Viruses envelope protein.

The term "expression vector" and "recombinant expression vector" as used herein refers to a DNA molecule, for example a plasmid or virus, containing a desired and appropriate nucleic acid sequences necessary for the expression of the recombinant peptide epitopes for expression in a particular host cell. As used herein "operably linked" refers to a functional linkage of at least two sequences. Operably linked includes linkage between a promoter and a second sequence, for example an nucleic acid of the present invention, wherein the promoter sequence initiates and mediates transcription of the DNA sequence corresponding to the second sequence.

The regulatory regions necessary for transcription of the peptide epitopes can be provided by the expression vector. The precise nature of the regulatory regions needed for gene expression may vary among vectors and host cells. Generally, a promoter is required which is capable of binding RNA polymerase and promoting the transcription of an operably-associated nucleic acid sequence. Regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites. A translation initiation codon (ATG) may also be provided.

In order to clone the nucleic acid sequences into the cloning site of a vector, linkers or adapters providing the appropriate compatible restriction sites are added during, synthesis of the nucleic acids. For example, a desired restriction enzyme site can be introduced into a fragment of DNA by amplification of the DNA by use of PCR with primers containing the desired restriction enzyme site.

An expression construct comprising a peptide epitope sequence operably associated with regulatory regions can be directly introduced into appropriate host cells for expression and production of the multimeric multiepitope polypeptide per se or as recombinant fusion proteins. The expression vectors that may be used include but are not limited to plasmids, cosmids, phage, phagemids, flagellin or modified viruses. Typically, such expression vectors comprise a functional origin of replication for propagation of the vector in an appropriate host cell, one or more restriction endonuclease sites for insertion of the desired gene sequence, and one or more selection markers.

The recombinant polynucleotide construct comprising the expression vector and a multimeric polypeptide should then be transferred into a bacterial host cell where it can replicate and be expressed. This can be accomplished by methods known in the art. The expression vector is used with a compatible prokaryotic or eukaryotic host cell which may be derived from bacteria, yeast, insects, mammals and humans.

Production of the Multimeric Polypeptide

Once expressed by the host cell, the multimeric polypeptide can be separated from undesired components by a number of protein purification methods. One such method uses a polyhistidine tag on the recombinant protein. A polyhistidine-tag consists in at least six histidine (His) residues added to a recombinant protein, often at the N- or C-terminus Polyhistidine-tags are often used for affinity purification of polyhistidine-tagged recombinant proteins that are expressed in E. coli or other prokaryotic expression systems. The bacterial cells are harvested by centrifugation and the resulting cell pellet can be lysed by physical means or with detergents or enzymes such as lysozyme. The raw lysate contains at this stage the recombinant protein among several other proteins derived from the bacteria and are incubated with affinity media such as NTA-agarose, HisPur resin or Talon resin. These affinity media contain bound metal ions, either nickel or cobalt to which the polyhistidine-tag binds with micromolar affinity. The resin is then washed with phosphate buffer to remove proteins that do not specifically interact with the cobalt or nickel ion. The washing efficiency can be improved by the addition of 20 mM imidazole and proteins are then usually eluted with 150-300 mM imidazole. The polyhistidine tag may be subsequently removed using restriction enzymes, endoproteases or exoproteases. Kits for the purification of histidine-tagged proteins can be purchased for example from Qiagen.

Another method is through the production of inclusion bodies, which are inactive aggregates of protein that may form when a recombinant polypeptide is expressed in a prokaryote. While the cDNA may properly code for a translatable mRNA, the protein that results may not fold correctly, or the hydrophobicity of the added peptide epitopes may cause the recombinant polypeptide to become insoluble. Inclusion bodies are easily purified by methods well known in the art. Various procedures for the purification of inclusion bodies are known in the art. In some embodiments the inclusion bodies are recovered from bacterial lysates by centrifugation and are washed with detergents and chelating agents to remove as much bacterial protein as possible from the aggregated recombinant protein. To obtain soluble protein, the washed inclusion bodies are dissolved in denaturing agents and the released protein is then refolded by gradual removal of the denaturing reagents by dilution or dialysis (as described for example in Molecular cloning: a laboratory manual, 3rd edition, Sambrook, J. and Russell, D. W., 2001; CSHL Press).

Vaccine Formulation

The vaccines of the present invention comprise a multi-epitope polypeptide or a recombinant fusion protein comprising a multi-epitope polypeptide, and optionally, an adjuvant. The vaccine can be formulated for administration in one of many different modes. In one embodiment, the vaccine is formulated for parenteral administration. In some embodiments the vaccine is formulated for mass inoculation, for example for use with a jet-injector or a single use cartridge. According to one embodiment of the invention, the vaccine administration is intramuscular. According to another embodiment the administration is intradermal. Needles specifically designed to deposit the vaccine intradermally are known in the art as disclosed for example in U.S. Pat. No. 6,843,781 and U.S. Pat. No. 7,250,036 among others. According to other embodiments the administration is performed with a needleless injector.

According to yet another embodiment the vaccine is administered intranasally. The vaccine formulation may be applied to the lymphatic tissue of the nose in any convenient manner. However, it is preferred to apply it as a liquid stream or liquid droplets to the walls of the nasal passage. The intranasal composition can be formulated, for example, in liquid form as nose drops, spray, or suitable for inhalation, as powder, as cream, or as emulsion. The composition can contain a variety of additives, such as adjuvant, excipient, stabilizers, buffers, or preservatives.

For straightforward application, the vaccine composition is preferably supplied in a vessel appropriate for distribution of the polypeptide or recombinant fusion protein in the form of nose drops or an aerosol. In certain preferred embodiments the vaccine is formulated for mucosal delivery, in particular nasal delivery (Arnon et al., Biologicals. 2001; 29(3-4):237-42; Ben-Yedidia et al., Int Immunol. 1999; 11(7):1043-51).

In another embodiment of the invention, administration is oral and the vaccine may be presented, for example, in the form of a tablet or encased in a gelatin capsule or a microcapsule. The formulation of these modalities is general knowledge to those with skill in the art.

Liposomes provide another delivery system for antigen delivery and presentation. Liposomes are bilayered vesicles composed of phospholipids and other sterols surrounding a typically aqueous center where antigens or other products can be encapsulated. The liposome structure is highly versatile with many types range in nanometer to micrometer sizes, from about 25 nm to about 50 µm. Liposomes have been found to be effective in delivering therapeutic agents to dermal and mucosal surfaces. Liposomes can be further modified for targeted delivery by for example, incorporating specific antibodies into the surface membrane, or altered to encapsulate bacteria, viruses or parasites. The average survival time or half life of the intact liposome structure can be extended with the inclusion of certain polymers, for example polyethylene glycol, allowing for prolonged release in vivo. Liposomes may be unilamellar or multilamellar.

The vaccine composition may be formulated by: encapsulating an antigen or an antigen/adjuvant complex in liposomes to form liposome-encapsulated antigen and mixing the liposome-encapsulated antigen with a carrier comprising a continuous phase of a hydrophobic substance. If an antigen/adjuvant complex is not used in the first step, a suitable adjuvant may be added to the liposome-encapsulated antigen, to the mixture of liposome-encapsulated antigen and carrier, or to the carrier before the carrier is mixed with the liposome-encapsulated antigen. The order of the process may depend on the type of adjuvant used. Typically, when an adjuvant like alum is used, the adjuvant and the antigen are mixed first to form an antigen/adjuvant complex followed by encapsulation of the antigen/adjuvant complex with liposomes. The resulting liposome-encapsulated antigen is then mixed with the carrier. The term "liposome-encapsulated antigen" may refer to encapsulation of the antigen alone or to the encapsulation of the antigen/adjuvant complex depending on the context. This promotes intimate contact between the adjuvant and the antigen and may, at least in part, account for the immune response when alum is used as the adjuvant. When another is used, the antigen may be first encapsulated in liposomes and the resulting liposome-encapsulated antigen is then mixed into the adjuvant in a hydrophobic substance.

In formulating a vaccine composition that is substantially free of water, antigen or antigen/adjuvant complex is encapsulated with liposomes and mixed with a hydrophobic substance. In formulating a vaccine in an emulsion of water-in-a hydrophobic substance, the antigen or antigen/adjuvant complex is encapsulated with liposomes in an aqueous medium followed by the mixing of the aqueous medium with a hydrophobic substance. In the case of the emulsion, to maintain the hydrophobic substance in the continuous phase, the aqueous medium containing the liposomes may be added in aliquots with mixing to the hydrophobic substance.

In all methods of formulation, the liposome-encapsulated antigen may be freeze-dried before being mixed with the hydrophobic substance or with the aqueous medium as the case may be. In some instances, an antigen/adjuvant complex may be encapsulated by liposomes followed by freeze-drying. In other instances, the antigen may be encapsulated by liposomes followed by the addition of adjuvant then freeze-drying to form a freeze-dried liposome-encapsulated antigen with external adjuvant. In yet another instance, the antigen may be encapsulated by liposomes followed by freeze-drying before the addition of adjuvant. Freeze-drying may promote better interaction between the adjuvant and the antigen resulting in a more efficacious vaccine.

Formulation of the liposome-encapsulated antigen into a hydrophobic substance may also involve the use of an emulsifier to promote more even distribution of the liposomes in the hydrophobic substance. Typical emulsifiers are well-known in the art and include mannide oleate (Arlacel™ A), lecithin, Tween™ 80, Spans™ 20, 80, 83 and 85. The emulsifier is used in an amount effective to promote even distribution of the liposomes. Typically, the volume ratio (v/v) of hydrophobic substance to emulsifier is in the range of about 5:1 to about 15:1.

Microparticles and nanoparticles employ small biodegradable spheres which act as depots for vaccine delivery. The major advantage that polymer microspheres possess over other depot-effecting adjuvants is that they are extremely safe and have been approved by the Food and Drug Administration in the US for use in human medicine as suitable sutures and for use as a biodegradable drug, delivery system (Langer R. Science. 1990, 249, 1527). The rates of copolymer hydrolysis are very well characterized, which in turn allows for the manufacture of microparticles with sustained antigen release over prolonged periods of time (O'Hagen, et al., Vaccine. 1993, 11, 965).

Parenteral administration of microparticles elicits long-lasting immunity, especially if they incorporate prolonged release characteristics. The rate of release can be modulated by the mixture of polymers and their relative molecular weights, which will hydrolyze over varying periods of time. Without wishing to be bound to theory, the formulation of different sized particles (1 µm to 200 µm) may also contribute to long-lasting immunological responses since large particles must be broken down into smaller particles before being available for macrophage uptake. In this manner a single-injection vaccine could be developed by integrating various particle sizes, thereby prolonging antigen presentation and greatly benefiting livestock producers.

In some applications an adjuvant or excipient may be included in the vaccine formulation. Montanide™ and alum for example, are preferred adjuvants for human use. The choice of the adjuvant will be determined in part by the mode of administration of the vaccine. For example, non-injected vaccination will lead to better overall compliance and lower overall costs. A preferred mode of administration is intramuscular administration. Another preferred mode of administration is intranasal administration. Non-limiting examples of intranasal adjuvants include chitosan powder, PLA and PLG microspheres, QS-21, calcium phosphate nanoparticles (CAP) and mCTA/LTB (mutant cholera toxin. E112K with pentameric B subunit of heat labile enterotoxin).

The adjuvant used may also be, theoretically, any of the adjuvants known for peptide- or protein-based vaccines. For example: inorganic adjuvants in gel form (aluminium hydroxide/aluminium phosphate, calcium phosphate, bacterial adjuvants such as monophosphoryl lipid A and muramyl peptides, particulate adjuvants such as the so-called ISCOMS ("immuno stimulatory complexes", liposomes and biodegradable microspheres, adjuvants based on oil emulsions and emulsifiers such as IFA ("Incomplete Freund's adjuvant"), SAF, saponines (such as QS-21), squalene/squalane, synthetic adjuvants such as non-ionic block copolymers, muramyl peptide analogs, synthetic lipid A, synthetic polynucleotides and polycationic adjuvants (WO 97/30721).

Adjuvants for use with immunogens of the present invention include aluminum or calcium salts (for example hydroxide or phosphate salts). A particularly preferred adjuvant for use herein is an aluminum hydroxide gel such as Alhydrogel™. Calcium phosphate nanoparticles (CAP) is an adjuvant being developed by Biosante, Inc (Lincolnshire, Ill.). The immunogen of interest can be either coated to the outside of particles, or encapsulated inside on the inside (He et al., 2000, Clin. Diagn. Lab. Immunol., 7, 899).

Another adjuvant for use with an immunogen of the present invention is an emulsion. A contemplated emulsion can be an oil-in-water emulsion or a water-in-oil emulsion. In addition to the immunogenic chimer protein particles, such emulsions comprise an oil phase of squalene, squalane, peanut oil or the like as are well known, and a dispersing agent. Non-ionic dispersing agents are preferred and such materials include mono- and di-$C_{12}$-$C_{24}$-fatty acid esters of sorbitan and mannide such as sorbitan mono-stearate, sorbitan mono-oleate and mannide mono-oleate.

Such emulsions are for example water-in-oil emulsions that comprise squalene, glycerol and a surfactant such as mannide mono-oleate (Arlacel™ A), optionally with squalane, emulsified with the chimer protein particles in an aqueous phase. Alternative components of the oil-phase include alpha-tocopherol, mixed-chain di- and tri-glycerides, and sorbitan esters. Well-known examples of such emulsions include Montanide™ ISA-720, and Montanide™ ISA 703 (Seppic, Castres, France. Other oil-in-water emulsion adjuvants include those disclosed in WO 95/17210 and EP 0 399 843.

The use of small molecule adjuvants is also contemplated herein. One type of small molecule adjuvant useful herein is a 7-substituted-8-oxo- or 8-sulfo-guanosine derivative described in U.S. Pat. No. 4,539,205, U.S. Pat. No. 4,643,992, U.S. Pat. No. 5,011,828 and U.S. Pat. No. 5,093,318. 7-allyl-8-oxoguanosine(loxoribine) has been shown to be particularly effective in inducing an antigen-(immunogen-) specific response.

A useful adjuvant includes monophosphoryl lipid A (MPL®), 3-deacyl monophosphoryl lipid A (3D-MPL®), a well-known adjuvant manufactured by Corixa Corp. of Seattle, formerly Ribi Immunochem, Hamilton, Mont. The adjuvant contains three components extracted from bacteria: monophosphoryl lipid (MPL®) A, trehalose dimycolate (TDM) and cell wall skeleton (CWS) (MPL+TDM+CWS) in a 2% squalene/Tween™ 80 emulsion. This adjuvant can be prepared by the methods taught in GB 2122204B.

Other compounds are structurally related to MPL® adjuvant called aminoalkyl glucosamide phosphates (AGPs) such as those available from Corixa Corp under the designation RC-529™ adjuvant {2-[(R)-3-tetra-decanoyloxytetradecanoylamino]-ethyl-2-deoxy-4-O-phosphon-o-3-O—[(R)-3-tetradecanoyloxytetra-decanoyl]-2-[(R)-3-tetra-decanoyloxytet-radecanoyl-amino]-p-D-glucopyranoside triethylammonium salt}. An RC-529 adjuvant is available in a squalene emulsion sold as RC-529SE and in an aqueous formulation as RC-529AF available from Corixa Corp. (see, U.S. Pat. No. 6,355,257 and U.S. Pat. No. 6,303,347; U.S. Pat. No. 6,113,918; and U.S. Publication No. 03-0092643).

Further contemplated adjuvants include synthetic oligonucleotide adjuvants containing the CpG nucleotide motif one or more times (plus flanking sequences) available from Coley Pharmaceutical Group. The adjuvant designated QS21, available from Aquila Biopharmaceuticals, Inc., is an immunologically active saponin fractions having adjuvant activity derived from the bark of the South American tree Quillaja Saponaria Molina (e.g. Quil™ A), and the method of its production is disclosed in U.S. Pat. No. 5,057,540. Derivatives of Quil™ A, for example QS21 (an HPLC purified fraction derivative of Quil™ A also known as QA21), and other fractions such as QA17 are also disclosed. Semi-synthetic and synthetic derivatives of Quillaja Saponaria Molina saponins are also useful, such as those described in U.S. Pat. No. 5,977,081 and U.S. Pat. No. 6,080,725. The adjuvant denominated MF59 available from Chiron Corp. is described in U.S. Pat. No. 5,709,879 and U.S. Pat. No. 6,086,901.

Muramyl dipeptide adjuvants are also contemplated and include N-acetyl-muramyl-L-threonyl-D-isoglutamine (thur-MDP), N-acetyl-nor-muramyl-L-alanyl-D-isoglutamine [CGP 11637, referred to as nor-MDP], and N-acetylmuramyl-L-alanyl-D-isoglutaminyl-L-alanine-2-(1'-2'-dipalmityol-s-n-glycero-3-hydroxyphosphoryloxy) ethylamine [(CGP) 1983A, referred to as MTP-PE]. The so-called muramyl dipeptide analogues are described in U.S. Pat. No. 4,767,842.

Other adjuvant mixtures include combinations of 3D-MPL and QS21 (EP 0 671 948 B1), oil-in-water emulsions comprising 3D-MPL and QS21 (WO 95/17210, PCT/EP98/05714), 3D-MPL formulated with other carriers (EP 0 689 454 B1), QS21 formulated in cholesterol-containing liposomes (WO 96/33739), or immunostimulatory oligonucleotides (WO 96/02555). Adjuvant SBAS2 (now ASO2) available from SKB (now Glaxo-SmithKline) contains QS21 and MPL in an oil-in-water emulsion is also useful. Alternative adjuvants include those described in WO 99/52549 and non-particulate suspensions of polyoxyethylene ether (UK Patent Application No. 9807805.8).

The use of an adjuvant that contains one or more agonists for toll-like receptor-4 (TLR-4) such as an MPL® adjuvant or a structurally related compound such as an RC-529® adjuvant or a Lipid A mimetic, alone or along with an agonist for TLR-9 such as a non-methylated oligo deoxynucleotide-containing the CpG motif is also optional.

Another type of adjuvant mixture comprises a stable water-in-oil emulsion further containing aminoalkyl glucosamine phosphates such as described in U.S. Pat. No. 6,113,918. Another water-in-oil emulsion is described in WO 99/56776.

Adjuvants are utilized in an adjuvant amount, which can vary with the adjuvant, host animal and immunogen. Typical amounts can vary from about 1. mcg to about 1 mg per immunization. Those skilled in the art know that appropriate concentrations or amounts can be readily determined.

Vaccine compositions comprising an adjuvant based on oil in water emulsion is also included within the scope of the present invention. The water in oil emulsion may comprise metabolisable oil and a saponin, such as for example as described in U.S. Pat. No. 7,323,182. The oil and a saponin are present, for example, in a ratio of between 1:1 and 200:1.

According to several embodiments, the vaccine compositions according to the present invention may contain one or more adjuvants, characterized in that it is present as a solution or emulsion which is substantially free from inorganic salt ions, wherein said solution or emulsion contains one or more water soluble or water-emulsifiable substances which is capable of making the vaccine isotonic or hypotonic. The water soluble or water-emulsifiable substances may be, for example, selected from the group consisting of: maltose; fructose; galactose; saccharose; sugar alcohol; lipid; and combinations thereof.

The formulations of the present invention may optionally comprise a mucosal delivery-enhancing agent such as for example a permeabilizing peptide that reversibly enhances mucosal epithelial paracellular transport by modulating epithelial junctional structure and/or physiology, as described in US 2004/0077540.

The multimeric multiepitope polypeptides used in the methods and compositions of the present invention comprise according to several specific embodiments a proteosome adjuvant. The proteosome adjuvant comprises a purified preparation of outer membrane proteins of meningococci and similar preparations from other bacteria. These proteins are highly hydrophobic, reflecting their role as transmembrane proteins and porins. Due to their hydrophobic protein-protein interactions, when appropriately isolated, the proteins form multi-molecular structures consisting of about 60-100 nm diameter whole or fragmented membrane vesicles. This liposome-like physical state allows the proteosome adjuvant to act as a protein carrier and also to act as an adjuvant. Polypeptides used according to the present invention are optionally complexed to the proteosome antigen vesicles through hydrophobic moieties. For example, an antigen is conjugated to a lipid moiety such as a fatty acyl group. Such a hydrophobic moiety may be linked directly to the multimeric polypeptide or alternatively, a short spacer, for example, of one, two, three or four, up to six or ten amino acids can be used to link the multimeric polypeptide to the fatty group. This hydrophobic anchor interacts with the hydrophobic membrane of the proteosome adjuvant vesicles, while presenting the generally hydrophilic antigenic peptide.

In particular, a hydrophobic anchor may comprise a fatty acyl group attached to the amino terminus or near the carboxyl terminus of the multimeric polypeptide. One example is the twelve-carbon chain lauroyl ($CH_3(CH_2)_{10}CO$), although any similarly serving fatty acyl group including, but not limited to, acyl groups that are of eight-, ten-, fourteen-, sixteen-, eighteen-, or twenty-carbon chain lengths can also serve as hydrophobic anchors. The anchor may be linked to the peptide antigen using an immunopotentiating spacer. Such a linker may consist of 1-10 amino acids, which may assist in maintaining the conformational structure of the peptide.

The two components, that is the multimeric polypeptide and proteosome adjuvant may be formulated by mixing of the components in a selected solution of detergent(s) and then removing the detergent(s) by diafiltration/ultrafiltration methods. In general, the ratio of proteosome adjuvant to multimeric polypeptide contained in the composition is preferably greater than 1:1 and may be, for example, 1:2, 1:3, 1:4 up to 1:5, 1:10 or 1:20 (by weight). The detergent-based solutions of the two components may contain the same detergent or different detergents and more than one detergent may be present in the mixture subjected to ultrafiltration/diafiltration. Suitable detergents include Triton, Empigen and Mega-10. Other suitable detergents can also be used. The detergents serve to solubilise the components used to prepare the composition.

Vaccines comprising different multimeric polypeptides can be produced by mixing, a number of different antigenic peptides with proteosome adjuvant. Alternatively, two or more proteosome adjuvant/antigenic peptide compositions can be produced and subsequently mixed.

The antigen content is best defined by the biological effect it provokes. Naturally, sufficient antigen should be present to provoke the production of measurable amounts of protective antibody. A convenient test for the biological activity of viruses involves the ability of the antigenic material undergoing testing to deplete a known positive antiserum of its protective antibody. The result is reported in the negative log of the $LD_{50}$ (lethal dose, 50%) for mice treated with virulent organisms which are pretreated with a known antiserum which itself was pretreated with various dilutions of the antigenic material being evaluated. A high value is therefore reflective of a high content of antigenic material which has tied up the antibodies in the known antiserum thus reducing or eliminating the effect of the antiserum on the virulent organism making a small dose lethal. It is preferred that the antigenic material present in the final formulation is at a level sufficient to increase the negative log of $LD_{50}$ by at least 1 preferably 1.4 compared to the result from the virulent organism treated with untreated antiserum. The absolute values obtained for the antiserum control and suitable vaccine material are, of course, dependent on the virulent organism and antiserum standards selected.

The following method may be also used to achieve the ideal vaccine formulation: starting from a defined antigen, which is intended to provoke the desired immune response, in a first step an adjuvant matched to the antigen is found, as described in the specialist literature, particularly in WO 97/30721. In a next step the vaccine is optimized by adding various isotonic-making substances as defined in the present inventions, preferably sugars and/or sugar alcohols, in an isotonic or slightly hypotonic concentration, to the mixture of antigen and adjuvant, with the composition otherwise being identical, and adjusting the solution to a physiological pH in the range from pH 4.0 to 10.0, particularly 7.4. Then, in a first step the substances or the concentration thereof which will improve the solubility of the antigen/adjuvant composition compared with a conventional, saline-buffered solution are determined. The improvement in the solubility characteristics by a candidate substance is a first indication that this substance is capable of bringing about an increase in the immunogenic activity of the vaccine.

Since one of the possible prerequisites for an increase in the cellular immune response is increased binding of the antigen to APCs (antigen presenting cells), in a next step an investigation can be made to see whether the substance leads to an increase of this kind. The procedure used may be analogous to that described in the definition of the adjuvant, e.g. incubating APCs with fluorescence-labelled peptide or protein, adjuvant and isotonic-making substance. An increased uptake or binding of the peptide to APCs brought about by the substance can be determined by comparison with cells which have been mixed with peptide and adjuvant alone or with a peptide/adjuvant composition which is present in conventional saline buffer solution, using throughflow cytometry.

In a second step the candidate substances may be investigated in vitro to see whether and to what extent their presence is able to increase the presentation of a peptide to APCs; the MHC concentration on the cells may be measured using the methods described in WO 97/30721 for testing peptides.

Another possible way of testing the efficiency of a formulation is by using an in vitro model system. In this, APCs are incubated together with adjuvant, peptide and candidate substance and the relative activation of a T-cell clone which specifically recognizes the peptide used is measured (Coligan et al., 1991; Lopez et al., 1993).

The efficiency of the formulation may optionally also be demonstrated by the cellular immune response by detecting a "delayed-type hypersensitivity" (DTH) reaction in immunized animals. Finally, the immunomodulatory activity of the formulation is measured in animal tests.

Synthetic Peptides and Analogs

The multimeric peptides and polypeptides of the present invention may be synthesized chemically using methods known in the art for synthesis of peptides, peptide multimers and polypeptides. These methods generally rely on the known principles of peptide synthesis; most conveniently, the procedures can be performed according to the known principles of solid phase peptide synthesis.

As used herein "peptide" indicates a sequence of amino acids linked by peptide bonds. The peptides according to the present invention comprise a sequence of 4 to 24 amino acid residues. Multimeric polypeptides comprise at least two repeats and maximum 50 repeats of the peptide epitopes.

Peptide analogs and peptidomimetics are also included within the scope of the invention as well as salts and esters of the peptides of the invention are encompassed. A peptide analog according to the present invention may optionally comprise at least one non-natural amino acid and/or at least one blocking group at either the C terminus or N terminus. Salts of the peptides of the invention are physiologically acceptable organic and inorganic salts. The design of appropriate "analogs" may be computer assisted.

The term "peptidomimetic" means that a peptide according to the invention is modified in such a way that it includes at least one non-peptidic bond such as, for example, urea bond, carbamate bond, sulfonamide bond, hydrazine bond, or any other covalent bond. The design of appropriate "peptidomimetic" may be computer assisted.

Salts and esters of the peptides of the invention are encompassed within the scope of the invention. Salts of the peptides of the invention are physiologically acceptable organic and inorganic salts. Functional derivatives of the peptides of the invention covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide and do not confer toxic properties on compositions containing it. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

The term "amino acid" refers to compounds, which have an amino group and a carboxylic acid group, preferably in a 1,2-1,3-, or 1,4-substitution pattern on a carbon backbone. α-Amino acids are most preferred, and include the 20 natural amino acids (which are L-amino acids except for glycine) which are found in proteins, the corresponding D-amino acids, the corresponding N-methyl amino acids, side chain modified amino acids, the biosynthetically available amino acids which are not found in proteins (e.g., 4-hydroxy-proline, 5-hydroxy-lysine, citrulline, ornithine, canavanine, djenkolic acid, β-cyanolanine), and synthetically derived α-amino acids, such as amino-isobutyric acid, norleucine, norvaline, homocysteine and homoserine. β-Alanine and γ-amino butyric acid are examples of 1,3 and 1,4-amino acids, respectively, and many others are well known to the art. Statine-like isosteres (a dipeptide comprising two amino acids wherein the CONH linkage is replaced by a CHOH), hydroxyethylene isosteres (a dipeptide comprising, two amino acids wherein the CONH linkage is replaced by a CHOHCH$_2$), reduced amide isosteres (a dipeptide comprising two amino acids wherein the CONH linkage is replaced by a CH$_2$NH linkage) and thioamide isosteres (a dipeptide comprising two amino acids wherein the CONH linkage is replaced by a CSNH linkage) are also useful residues for this invention.

The amino acids used in this invention are those, which are available commercially or are available by routine synthetic methods. Certain residues may require special methods for incorporation into the peptide, and sequential, divergent or convergent synthetic approaches to the peptide sequence are useful in this invention. Natural coded amino acids and their derivatives are represented by three-letter codes according to IUPAC conventions. When there is no indication, the L isomer was used.

Conservative substitutions of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I). Leucine (L), Methionine (M), Valine (V); and
6) Phenylalanine (F), Tyrosine (Y), Tryptophan (W).

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Multimeric Multiepitope Polypeptides:

Multimeric multiepitope polypeptides comprising several repeats of the influenza virus peptide epitopes E1 to E9 listed in Table 1 were produced and tested. The polypeptides include amino acids and short peptides as spacers. The polypeptides are arranged in an alternating sequential polymeric structure or a block copolymer structure. The polypeptides are prepared by expression in an expression vector from a polynucleotide construct comprising various restriction sites for further manipulation of the polypeptide. The polynucleotide construct is supplied from a commercial source.

Vaccines prepared from the multimeric multiepitope polypeptides were used for immunization studies of various mouse models and in clinical trials in human subjects.

A multimeric polypeptide with three repeats of each of nine different epitopes arranged in block copolymer structure $[E1]_3$-$[E2]_3$-$[E3]_3$-$[E4]_3$-$[E5]_3$-$[E6]_3$-$[E7]_3$-$[E8]_3$-$[E9]_3$, was produced and denoted M-001. The estimated molecular weight of M-001 is 48 kD. The amino acid sequence of the M-001 multimeric polypeptide is:

```
                                            (SEQ ID NO: 86)
MHMRSPAKLLKERGFFGAIAGFLEPPAKLLKERGFFGAIAGFLEPPAKL

LKERGFFGAIAGFLEPSKAYSNCYPYDVPDYASLPSKAYSNCYPYDVPD

YASLPSKAYSNCYPYDVPDYASLPSLLTEVETYVLSLLTEVETYVLSLL

TEVETYVLWLTGKNGLYPWLTGKNGLYPWLTGKNGLYPWTGVTQNPWTG

VTQNPWTGVTQNPFWRGENGRKTRSAYERMCNILKGKPFWRGENGRKTR

SAYERMCNILKGKPFWRGENGRKTRSAYERMCNILKGKPPKYVKQNTLK

LATPPKYVKQNTLKLATPPKYVKQNTLKLATPSAAFEDLRVLSFIRGYP
```

-continued

SAAFEDLRVLSFIRGYPSAAFEDLRVLSFIRGYPELRSRYWAIRTRSGP

ELRSRYWAIRTRSGPELRSRYWAIRTRSG.

The DNA sequence of the polynucleotide construct used to prepare the M-001 multimeric peptide is:

(SEQ ID NO: 85)
ATGCATATGAGATCTCCAGCTAAACTTCTGAAAGAACGTGGATTTTCG

GTGCAATCGCTGGTTTTCTGGAGCCACCGGCGAAGCTGCTGAAAGAACG

TGGGTTCTTCGGTGCGATTGCCGGTTTCTTGGAACCTCCCGCGAAACTT

CTGAAAGAGCGGGGCTTCTTTGGAGCGATTGCGGGCTTCTTGGAGCCAT

CGAAAGCCTACAGTAACTGTTACCCCTACGATGTGCCCGATTATGCCAG

CCTGCCTTCAAAAGCGTATTCGAACTGCTACCCGTATGATGTGCCAGAT

TACGCCAGCCTGCCAAGCAAAGCCTACTCTAATTGTTACCCATACGATG

TGCCTGATTATGCGAGCCTCCCTAGCCTCCTTACAGAAGTTGAAACTTA

TGTGCTCAGCTTGCTGACAGAAGTGGAAACCTACGTTCTCAGCTTGCTG

ACAGAAGTGGAAACCTACGTTCTCTGGCTGACAGGGAAAAACGGCCTTT

ATCCTTGGCTGACCGGTAAGAACGGTCTGTATCCGTGGCTGACGGGCAA

AAATGGTCTCTACCCATGGACCGGCGTGACGCAGAACCCTTGGACTGGT

GTGACACAAAACCCATGGACCGGAGTTACCCAGAATCCTTTCTGGCGTG

GCGAAAATGGACGTAAAACTCGCAGTGCGTATGAGCGCATGTGTAACAT

CCTCAAAGGTAAACCCTTTTGGCGGGGGAAAACGGCCGGAAAACCCGC

AGCGCTTACGAGCGCATGTGCAACATTCTGAAAGGCAAACCATTCTGGC

GCGGTGAGAACGGCCGTAAAACACGTTCAGCGTACGAGCGGATGTGCAA

CATCTTAAAAGGCAAACCTCCGAAATACGTGAAGCAGAATACGCTCAAA

CTTGCCACGCCACCGAAATACGTCAAGCAGAATACTCTGAAGTTAGCCA

CTCCGCCGAAATACGTCAAGCAGAATACTCTGAAGTTAGCCACTCCTTC

AGCCGCCTTTGAAGACCTTCGCGTCTTGAGTTTTATCCGGGGTTATCCA

AGCGCAGCCTTTGAAGACCTGCGGGTCTTGAGCTTTATCCGCGGTTACC

CTTCAGCCGCCTTTGAAGACCTTCGCGTCTTGAGTTTTATCCGGGGTTA

TCCAGAACTGCGTTCTCGCTATTGGGCGATCCGTACCCGGTCAGGGCCG

GAGCTGCGGTCGCGCTACTGGGCGATTCGTACGCGTAGTGGTCCAGAAC

TGCGGAGCCGCTACTGGGCTATTCGTACGCGGTCGGGTTAATAACTCGA

GAGGCTTTCTAGACA'TATGATGCAT.

Seasonal Influenza Vaccine

The commercial trivalent (TIV) vaccine Vaxigrip® of Sanofi Pasteur was used as an example of seasonal vaccine. Vaxigrip® is an inactivated trivalent influenza vaccine containing types A and B (split virion). Vaxigrip®, is approved for a single immunization in human. An ordinary dose or the indicated fraction of an ordinary dose, of Vaxigrip® for the mentioned season was used in each trial.

Adjuvant

Adjuvant used in clinical trials was IFA in animal studies and Montanide™ ISA 51 VG (Seppic, France) in human trials. Montanide™ is a commonly used immune modulator that has been employed in many clinical trials testing vaccine efficacy, capable of inducing both cellular and humoral immune responses (Peek et al., Adv Drug Deliv Rev. 2008; 60, 915-928).

Analysis of Immune Response

Analysis included humoral and cellular responses of M-001-immunized subjects in relation to their basal reactivity to the vaccine, to its peptide components or to whole Influenza viruses. Humoral immunity was determined by measuring IgG levels and by testing complement mediated lysis. Cellular response was evaluated via determination of proliferation of specific immune-related cells and TH1 cytokines secretion from these cells.

Humoral Response Endpoint

In order to evaluate antigenicity of M-001, antibody levels and their specificity were measured on day 42 of the BVX-003 study (example 4). Immune responses were also evaluated on day 63, approximately 21 days after administration of the seasonal influenza vaccine, among those subjects participating in the voluntary arm of the study. This arm of the study was designed to compare subject responses to the seasonal influenza vaccine administered on an immune background influences by the active M-001 vaccinations to those of subjects treated earlier with placebo solutions. Significance of humoral responses was determined by measuring the degree of reactivity of several antibodies to antigens of interest on a predetermined post-vaccination day, and compared to that measured at the start of the study (day 0). The assay background value was set at the optical density measured in ELISA-plate wells without sera, which was then subtracted from all assay values. M-001 (50 ng/well), whole influenza virus (1-20HAU/well) or influenza peptide (25 ng/well)-coated ELISA plates were used to determine sera antibody specificity and anti-antigen reactivity above background.

Hemagglutination Inhibition Assay (HAI):

HAI assay is considered by the regulatory authorities a correlate for protection against influenza. A positive result is when the HAI titer is ≥40. The M-001 contains epitopes from the inner hidden regions of the HA and hence, does not induce HAI Abs, however, after immunization with the seasonal vaccine these Abs are found. HAI Abs are highly specific to influenza strains, we tested the HAI towards influenza viruses included in the Vaxigrip® for 2009/2010 season (A/Brisbane/59/2007 (H1N1), A/Brisbane/10/2007 (H3N2) and B/Brisbane/60/2008 (Victoria lineage)) and other viruses to show the universality of the response following priming with the M-001.

Serial two-fold dilutions of serum collected from vaccinated subjects are incubated with the test viruses to determine the dilution at which inhibition of unbound erythrocyte agglutination no longer occurs. The reciprocal of the dilution at which this occurs is then defined as the HAI titer. Subjects were considered seroconverted toward a specific influenza virus when the fold increase in HAI titers was ≥4-fold that of baseline titers as measured in sera collected on day 0 of the study and diluted 1:10. In trial. BVX-3 for example, a subject was considered seroprotected when expressing HAI titers of ≥40 on day 63 of the study. Geometric mean titer ratios (GMT) were also calculated to express the relation between post-vaccination vs. pre-vaccination HAI titers.

Example 1

Prime-Boost Study in Mice

The objective of this study was to determine priming effect of the M-001 vaccine in mice and the ability of the multimeric polypeptide to enhance the humoral response to a commercial trivalent vaccine.

Transgenic female HHD++2 mice 10-12 weeks old were immunized twice IM with M-001 adjuvanted 1:1 in IFA (50 µl/limb total of 100 µl/mouse). Two mice per group (showing the higher humoral immunity to M-001) were further immunized with a third immunization to follow their cellular immune responses in spleen and lymph nodes lymphocytes. Apart from these couples of mice, the rest of each group was boosted with 1.5% (0.675 mcg/50 microliter/mouse) of an ordinary dose of Vaxigrip® for season 2009/2010, containing, the following three viruses: A/Brisbane/59/2007 (H1N1), A/Brisbane/10/2007 (H3N2), and B/Brisbane/60/2008. The HAI responses to the three Brisbane strains that are included in the vaccine and also to the drifting A/New Caledonia/20/99 H1N1 virus strain were measured.

Figure 4:
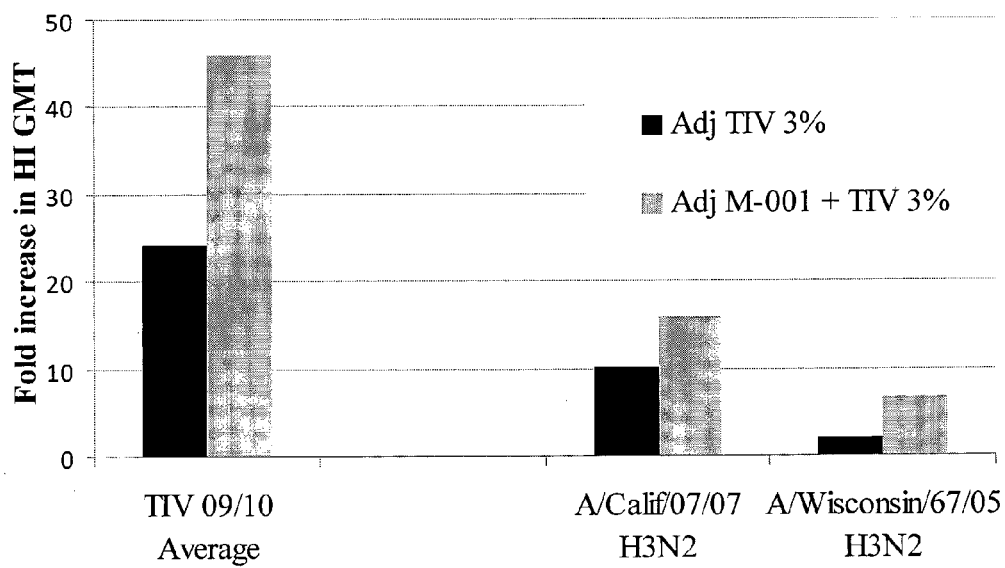
Figure 5:
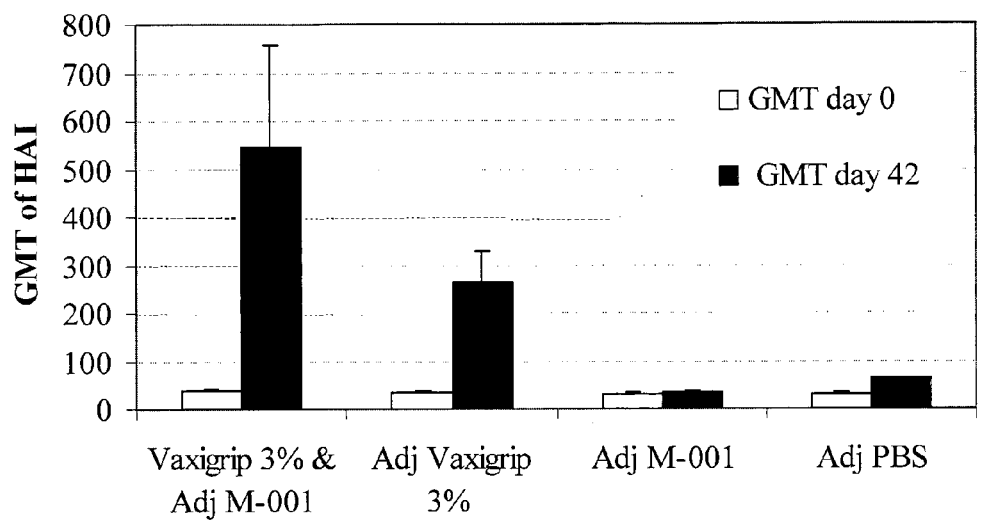
Figure 6:
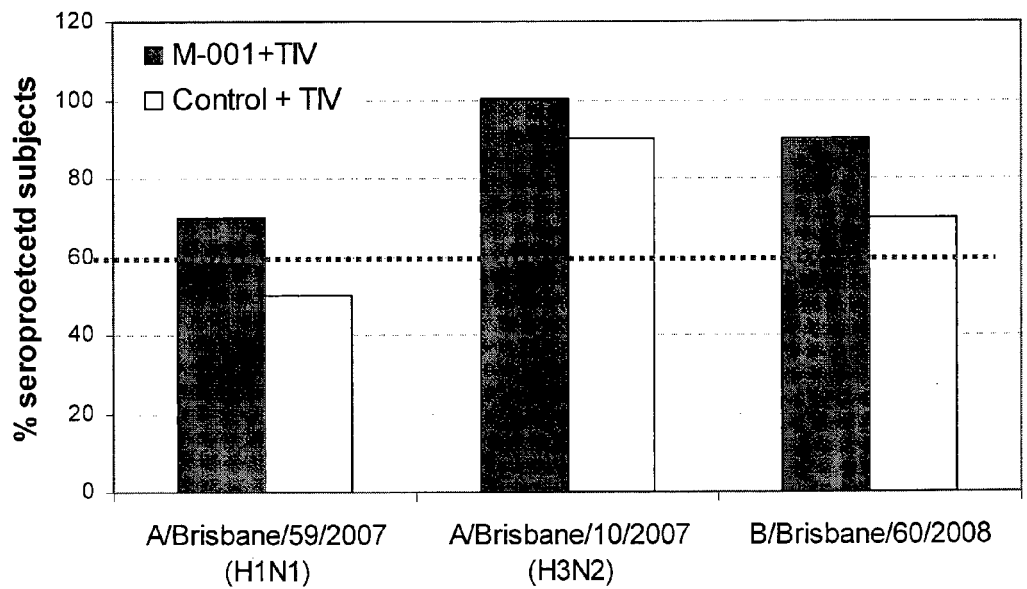

As expected, two immunizations with M-001 alone did not elicit HAI antibodies. Priming potential of the M-001 polypeptide, in terms of enhanced percentage of mice with elevated HAI was demonstrated for all viruses present in the Vaxigrip® 2009/2010 vaccine and also for the A/New Caledonia/20/99 that is not included in this specific seasonal composition. FIG. 1 demonstrates improved Homologous H1N1 HAI response to lower-dose TIV (Vaxigrip) after administration of M-001 to mice. Average ratio of HAI 14 days after immunization with 1.5% of standard Vaxigrip dose compared to HAI titer on day 0 (baseline), in mice that had previously received either M-001 or placebo. HAI measured by A/New Caledonia/20/99 H1N1 virus, a strain included in the administered Vaxigrip. Error bars denote SE.

Example 2

Prime-Boost Study in Mice

Objective: to evaluate the M-001 vaccine potential in priming immune responses in mice by comparing humoral responses induced by immunization with M-001 vaccine followed by immunization with a commercial trivalent influenza vaccine; and to evaluate protection following immunization with the M-001 vaccine alone or with a combination of M-001 and a commercial trivalent vaccine.

Materials: Vaxigrip® for season 2005/2006, includes 7.5 μg of HA from each of the following strains: A/New Caledonia/20/99 (H1N1), A/California/7/2004 (H3N2) and B/Shanghai/36/2002, in one 0.25 ml human dose. M-001: (insoluble protein), 5 mg/ml, diluted to 300 mcg/100 microliter with PBS following sonication, and emulsified 1:1 in IFA before injection.

Method: Female HHD++2 mice 10-12 weeks old were immunized intra muscularly on days 0, 21 and 42; Volume for IM administration: Vaxigrip® (1:10 with PBS): 50 μl/limb total of 50 μl/mouse; Multimeric: total of 150 μg/100 μl/administration; PBS: total of 50 μl/mouse. Blood samples were collected on day 0, 35, and 56.

Experiment Schedule:

| Day No. (±1 day) | | 0 | 21 | 35 | 42 | 56 |
|---|---|---|---|---|---|---|
| Immunization | Group 1 | PBS | PBS | | Vaxigrip ® | |
| | Group 2 | M-001 | M-001 | | Vaxigrip ® | |
| | Group 3 | PBS | M-001 | | Vaxigrip ® | |
| | Group 4 | PBS | PBS | | PBS | |
| Clinical Examination | | ✓ | ✓ | ✓ | ✓ | ✓ |
| Bleeding for serology | | ✓ | | ✓ | | ✓ |

Clinical examination includes evaluation of weight loss, pilo-erection, hunched posture, reduced mobility and other relevant clinical signs of distress by observation. Mice demonstrating signs of distress and morbidity as above are deemed to have met experimental endpoint criteria and are not euthanized.

Results: seroprotection to strain A/New Caledonia/20/99, not included in the TIV vaccine, is shown after priming with M-001 and boosting with Vaxigrip® 2009/2010 containing the 3 Brisbane strains. FIG. 2 demonstrates improved Seroprotection against heterologous flu in mice primed with one or two doses of M-001. Percent seroprotection against heterologous influenza strain (A/NC/20/99) after priming with M-001 and boosting with Vaxigrip 2009/2010, a formulation that lacks HA derived from strain A/NC/20/99.

Example 3

Twice Co-Administration of M-001 with Vaxigrip® in Mice

Objective: To evaluate enhancement of humoral (antibody) response (HAI) to a commercial seasonal trivalent vaccine by co-administration with M-001; to determine HAI to viruses included in the 2009/2010 Vaxigrip™ following co-administration with M-001 vaccine; and to determine HAI to viruses not included in the 2009/2010 Vaxigrip® following co-administration with M-001 vaccine.

Materials: Multimeric M-001 after microfluidizer using a microfluidizer apparatus (microfluidics, Boston, US), particle size: <8 μm, 150 μg/administration 1:1 in IFA; PBS as placebo; adjuvant: IFA included in all tested groups as 1:1 dilution. Vaxigrip® for 2009/2010 season (batch E7024) containing 15 mcg of HA of the following viruses: A/Brisbane/59/2007 (H1N1), A/Brisbane/10/2007 (H3N2), B/Brisbane/60/2008. Female outbred ICR mice 10-12 weeks old (8 mice per group) were used.

Protocol: a single IM injection on day 0 and 14 according to the schedule below of a composition selected from: M-001; M-001+Vaxigrip® 2009/2010 3%; PBS. Blood samples are collected on days −4, 0, 14 and 28.

Experiment Schedule:

| Day No. (±1day) | | −4 | 0 | 14 | 28 | 43 |
|---|---|---|---|---|---|---|
| Immunization | Group 1 | | M-001 + VaxiGrip ® 3% | M-001 + Vaxigrip ® 3% | | |
| | Group 2 | | M-001 | M-001 | | |
| | Group 3 | | PBS | PBS | | |
| | Group 4 | | PBS + Vaxigrip ® 3% | PBS + Vaxigrip ® 3% | | |
| Clinical Examination | | ✓ | ✓ | ✓ | ✓ | ✓ |
| Bleeding for serology | | ✓ | ✓ | ✓ | ✓ | |

Results: An improved response was observed to the Brisbanes strains contained within the seasonal vaccine (FIG. 3) and also to other viruses not included in the commercial seasonal vaccine (FIG. 4). In some cases the minimal dose of TIV was sufficient to induce seroconversion in all mice even without the mulmiteric priming, yet, an improved GMT was found (FIG. 5).

Figure 3:
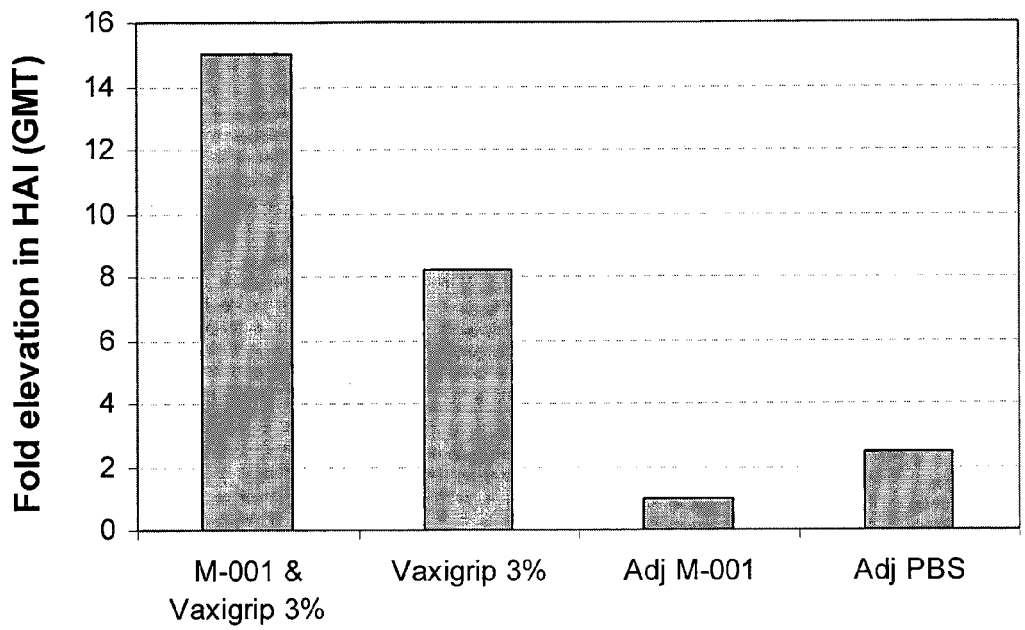
Figure 7:
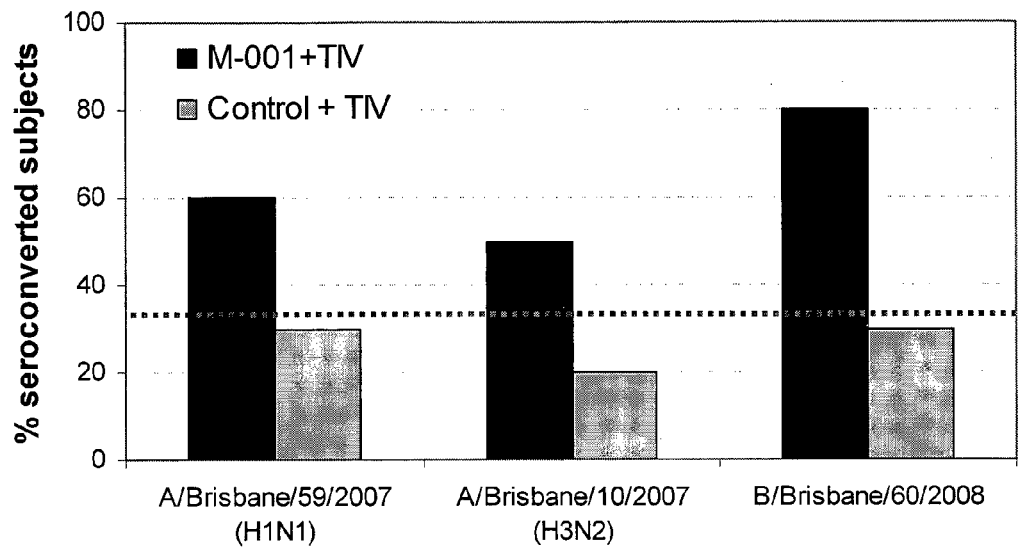

FIG. 3 depicts improved Homologous H1N1 HAI responses to very low-dose of TIV after administration of outbred mice with M-001. HAI response in outbred ICR mice to homologous strain A/Brisbane/59/2007 (H1N1) after 2 low dose (3%) administrations with Vaxigrip containing HA derived from the same H1N1 strain. FIG. 4 shows improved homologous and heterologous HAI responses in outbred mice elicited by low-dose TIV after administration of M-001. Homologous and heterologous HAI responses after 2 immunizations of ICR mice with Vaxigrip containing HA derived from a viral strain included in the vaccine (left column) and to two virus strains not included in the seasonal. FIG. 5 demonstrates improved homologous responses to A/Brisbane/59/20 in outbred mice. HAI GMT homologous responses of ICR mice to A/Brisbane/59/2007 (H1N1) after 2 IM low-dose injections with Vaxigrip.

Example 4

BVX-003-Phase I/II Trial in Elderly Human Subjects

A phase I/II, randomized, single-blind, placebo-controlled escalating double-dose, safety and priming potential study of M-001 injected IM to elderly volunteers.

Objectives: Assessment of the safety, tolerability, and reactogenicity of the adjuvanted and non-adjuvanted M-001 vaccine, when administered twice, intramuscularly to elderly male and female subjects; characterization of the immune response induced by single and repeated (two) intramuscular administrations of M-001 and of adjuvanted M-001; providing necessary data to determine relevant markers and efficacy protocols for future clinical studies; obtaining preliminary information on the influence of adjuvant on safety, tolerability and immunogenicity of the different vaccine doses; and evaluating the priming effect of the M-001 vaccine when administered prior to vaccination with a whole dose of conventional trivalent seasonal influenza vaccine.

Materials: Caucasian males and females, ages 55-75, healthy or with medically-controlled hypertension and/or hyperlipidemia were included in the trial. The water in oil emulsion Montanide™ ISA 51VG adjuvant was used. A whole dose of 45 μg/0.5 ml of trivalent vaccine recommended by Israeli health authorities for the 2009/2010 season (Vaxigrip™) was administered to participants who were not immunized with any "seasonal" influenza vaccine prior to screening. Multimeric polypeptide: M-001 in two doses: 250 μg (M250) and 500 μg (M500) prepared in PBS. PBS and adjuvanted PBS served as placebo, administered intramuscularly at the same volumes (0.2 ml) and schedules (2 administrations at 21 days intervals) as the active vaccine.

Methodology: Two intramuscular (IM) administrations, separated by a 21±2-day interval, of vaccine or placebo, prepared with or without adjuvant, into the deltoid muscle. Blood samples were collected for safety and immunogenicity evaluations. Eligible subjects were randomized to one of the six cohorts listed below, comprised of ten (10) subjects each. Each subject received the same formulation and dose at each of the two vaccination sessions (0.2 mL volume/session).

1. M250: 250 μg Mutlimeric-001 prepared in PBS.
2. M500: 500 μg Mutlimeric-001 prepared in PBS.

3. Adj M250: 250 μg Mutlimeric-001 prepared in Adjuvant.
4. Adj M500: 500 μg Mutlimeric-001 prepared in Adjuvant.
5. PBS: Placebo.
6. Adj: Adjuvant+PBS.

Participants not immunized before the study with the Winter 2009/2010 trivalent influenza vaccine, were offered the opportunity at the completion of the study (i.e. on day 42 which is 21 days after the second M-001 immunization). Immune responses of these subjects were evaluated 21 days after vaccination, namely, on day 63. Blood samples were collected for safety and immunogenicity evaluations on Days 0 and 42 and 63, for those subjects participating in the voluntary arm of the study.

Humoral and cellular immunological responses specific to M-001, influenza viruses and to the individual peptides included in the vaccine were determined. IgG levels specific to the M-001 protein, to whole influenza virus strains and to individual influenza virus peptides were measured by means of ELISA assays. In addition, HAI was measured and antibody-mediated cytotoxicity of M-001 immunized-sera was assessed against influenza virus-infected MDCK cells. Cellular stimulation was determined via monitoring of lymphocyte proliferation as well as quantification of IL-2 and IFN-γ levels in supernatants of isolated PBMCs of each subject upon their incubation with M-001, influenza viruses or influenza-specific epitopes.

Titers of hemagglutinin (HA)-specific IgG antibodies were measured via the Haemagglutinin Inhibition (HAI) assay and compared to those of placebo-treated subjects (never previously exposed to M-001). Serial two-fold dilutions of serum collected from vaccinated subjects were incubated with three test viruses comprising the seasonal influenza virus vaccine (A/Brisbane/59/2007 (H1N1), A/Brisbane/10/2007 (H3N2) and B/Brisbane/60/2008) to determine the dilution at which inhibition of unbound erythrocyte agglutination no longer occurs. The reciprocal of the dilution at which this occurs is then defined as the serial HAI titer. Subjects were considered seroconverted toward a specific influenza virus when the fold increase in HAI titers was ≥4-fold that of baseline titers as measured in sera collected on day 0 of the study and diluted 1:10. A subject was considered seroprotected when expressing HAI titers of ≥40 on day 63 of the study. Geometric mean titer ratios (GMT) were also calculated to express the relation between post-vaccination vs. pre-vaccination HAI titers.

Statistics: Fisher's Exact test was applied for testing the statistical significance of the differences in the rate of responders between the study groups. Analysis of Variance (ANOVA) using Dunnett method was applied for comparing the change from day 0 to day 42 between each of the study groups to the reference group PBS, and for comparing the change from day 0 to day 42 63 with adjustment of alpha to multiple comparisons.

Results: FIGS. 6 and 7 demonstrates improved efficacy, in terms of seroconversion and seroprotection, respectively, as measured by HAI, of subjects primed with M-001 as compared to subjects who were immunized with the seasonal vaccine only, to viruses that are included in the vaccine. FIG. 6 shows improved homologous HAI responses to virus strains included in the TIV seasonal vaccine after priming with M-001 prior to immunizing adults with standard TIV. HAI titers against A/Brisbane/59/2007, A/Brisbane/10/2007 and B/Brisbane/60/2008 were determined in sera of persons who previously had been administered either 250 mcg adjuvanted M-001 or placebo (adjuvanted PBS). Percent of seroprotected subjects was calculated as the number of subjects per cohort expressing an HAI titer ≥40 post immunization with TIV. Seroprotection level of 60% (the minimal post vaccination proportion of the elderly population needed for regulatory approval) is marked by a dashed line. Note that for H1N1 responses, improvement was particularly significant since the percent seroconversion among subjects receiving M-001 was greater than the level required for regulatory approval whereas seroconversion among persons given placebo prior to TIV was below that level. FIG. 7 demonstrates improved homologous HAI titres in elderly humans immunized with the TIV seasonal vaccine after priming with M-001. Serum HAI titers against A/Brisbane/59/2007, A/Brisbane/10/2007 and B/Brisbane/60/2008 in subjects administered either 250 mcg adjuvanted M-001 or placebo (adjuvanted-PBS). Percent of seroconverted subjects was calculated as the number of subjects per cohort expressing a mean fold increase in serum HAI Ab levels 40 post immunization with TIV. Seroconversion level of 30% (the minimal post vaccination proportion of the elderly population needed for regulatory approval) is marked by a dashed line. Note that the rate of seroconversion was markedly improved by priming with M-001 for all 3 strains examined.

Figure 8:
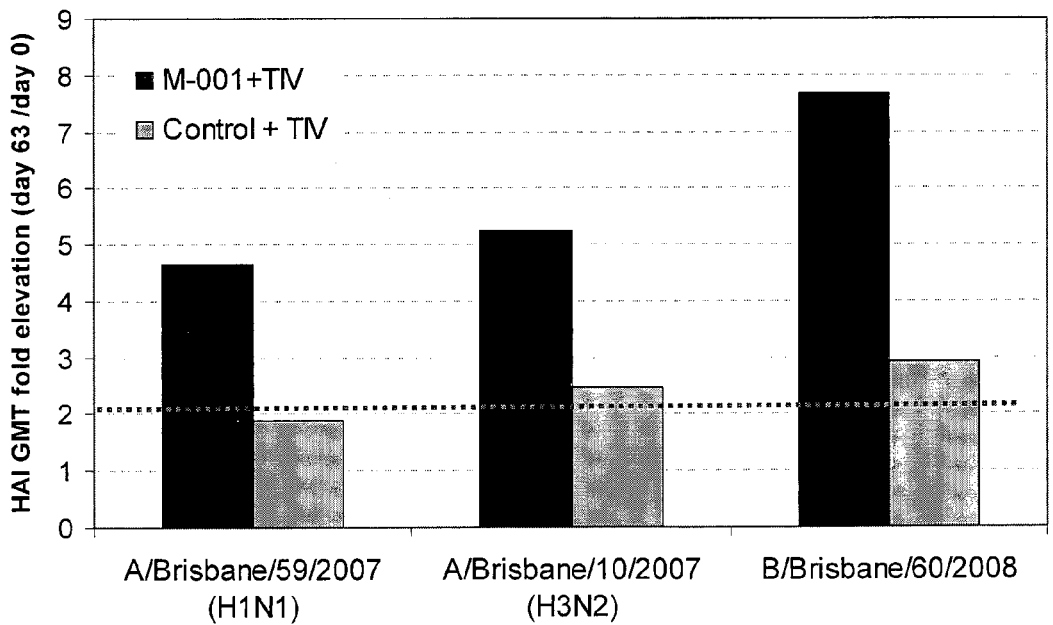

FIG. 8 shows HAI GMT values of the same subjects Indicating improved Homologous Serum HAI responses in persons primed with M-001 prior to immunization with standard TIV. Fold increases in HAI GMT in post-immunization human sera (day 63) compared to the HAI GMT on day 0. Increased GMT level of 2 (the minimal post vaccination proportion of the elderly population needed for regulatory approval) is marked by a dashed line.

Figure 9:
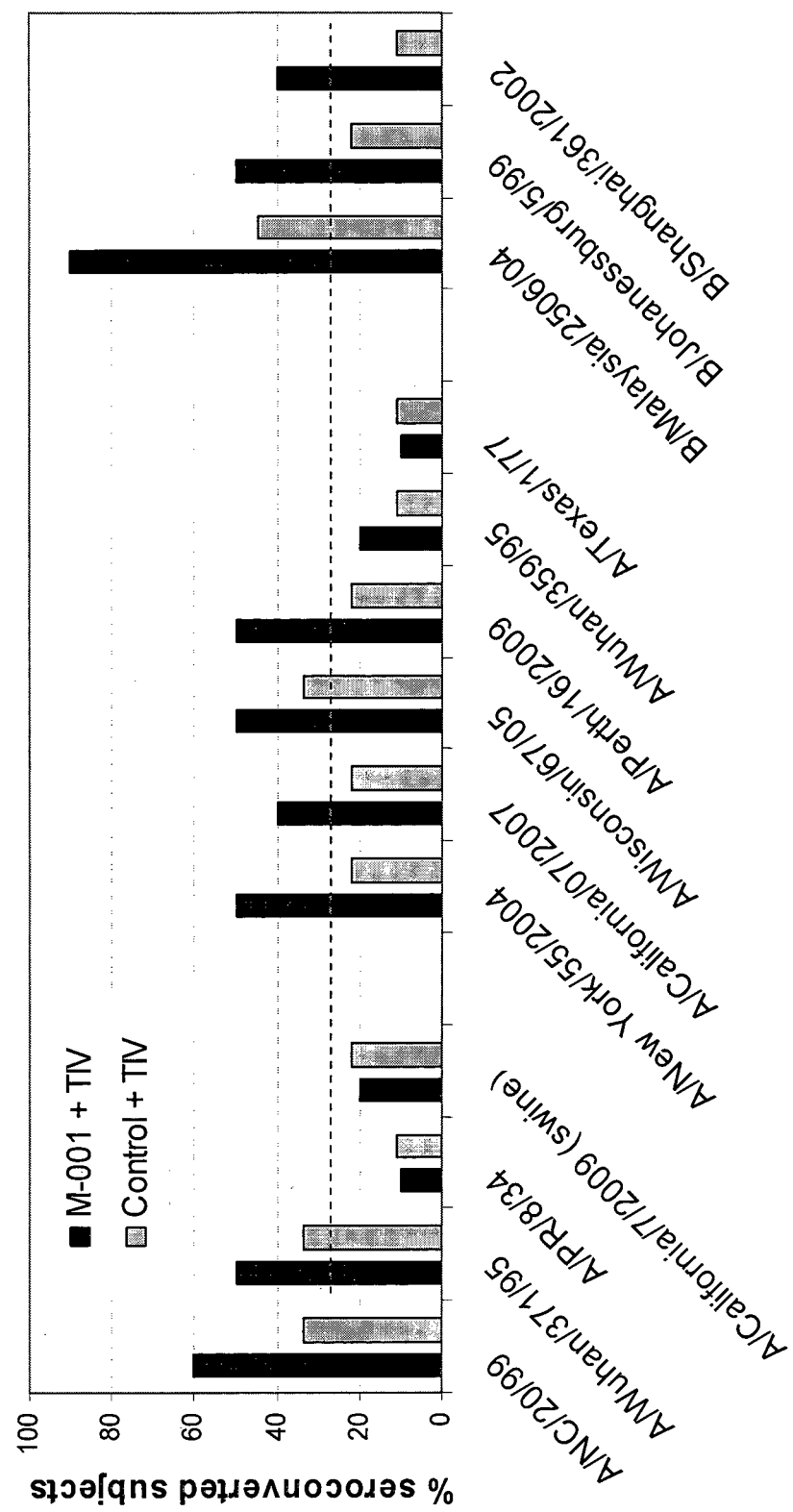
Figure 10:
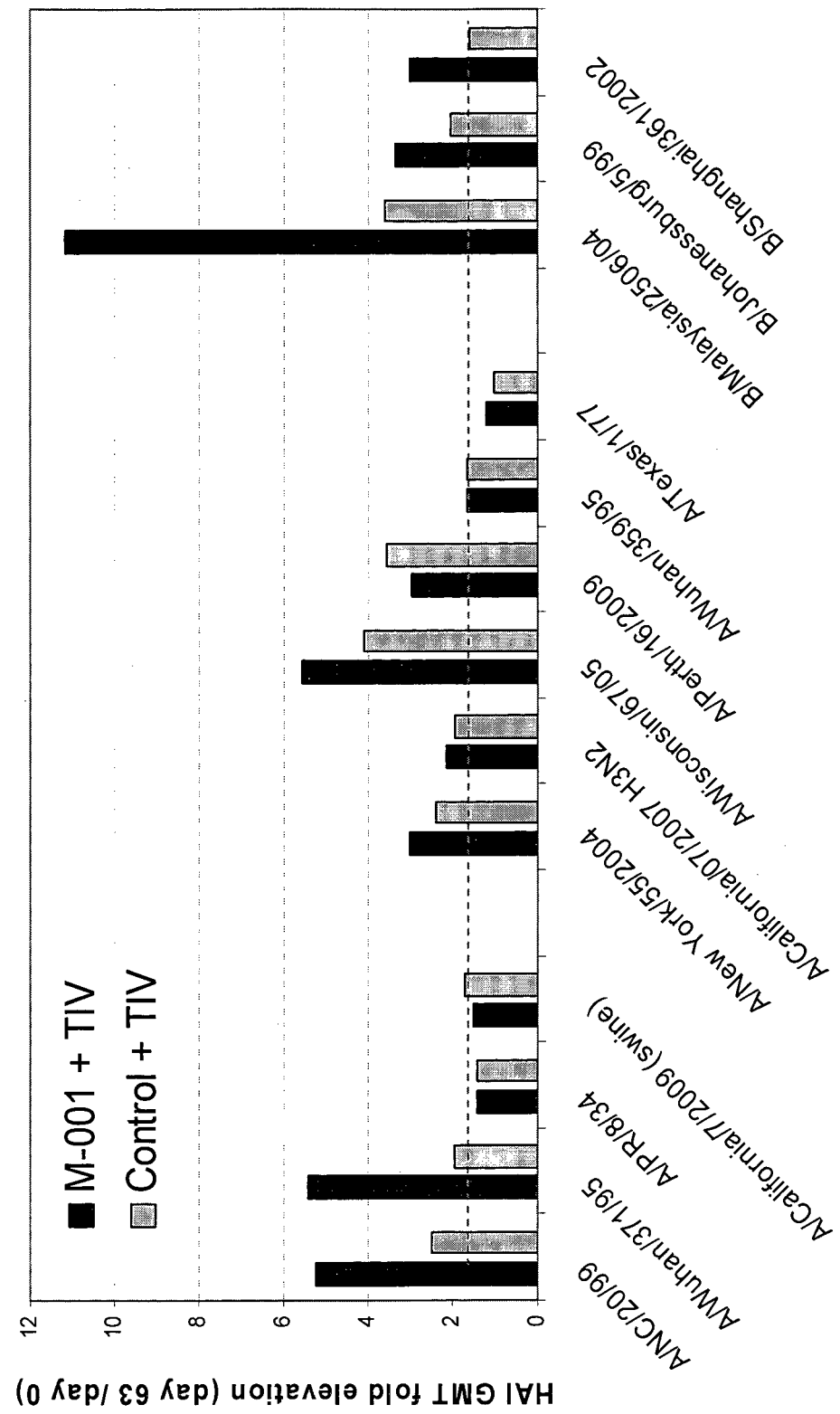

Unexpectedly, the efficacy of the seasonal vaccine (measured by HAI seroconversion FIGS. 9 and 10) to other viruses that are not included in the vaccine, was enhanced in 10 of 13 viruses tested. This enhancement was demonstrated in strains H1N1, H3N2 and in B strains from both Victoria and Yamagata lineages. In FIG. 9 improved Heterologous Serum HAI responses in persons primed with M-001 prior to immunization with standard TIV is demonstrated as improved % seroconversion. Improved HAI titres recognizing drifting virus strains that were not included in the seasonal TIV vaccine administered. HAI antibodies recognizing 10 of 13 historic influenza strains tested were improved in sera of elderly subjects primed with 250 mcg adjuvanted M-001 were improved compared to elderly subjects administered the adjuvanted placebo controls. Administering the adjuvanted PBS control did not result in such improved responses to any of the strains tested. Percent of seroconverted subjects was calculated as the number of subjects per cohort expressing a mean fold increase in HAI Ab levels of ≥4-fold from levels detected in sera collected on day 0 and titer ≥40 post immunizations. Seroconversion level of 30% (the minimal post vaccination proportion of the elderly population needed for regulatory approval) is marked by a dashed line. FIG. 10 discloses improved Heterologous Serum HAI responses in persons primed with M-001 prior to immunization with standard TIV as fold increases in HAI. HAI titres recognizing drifting virus strains that were not included in the seasonal TIV vaccine administered were improved in sera of persons primed with 250 mcg adjuvanted M-001 compared to persons administered the adjuvanted placebo controls. Increased GMT level of 2 (the minimal post vaccination proportion of the elderly population needed for regulatory approval) is marked by a dashed line.

For H1N1 (A/Brisbane/59/2007) and B (B/Brisbane/60/2008) viruses, the baseline GMT is higher in the Adj M500 group as compared to the other groups and hence, it seems that their response is lower than the others, however, when looking at the GMT on day 63, their GMT is comparable to the other groups. A significant proportion of participants primed with Adj M250 or M500 or M250 show seroconversion to all 3 viruses within the Vaxigrip® which is higher than the proportion of seroconverted subjects in the group primed with Adj PBS that were further immunized with the Vaxigrip®.

Safety: M-001 administration, alone or prior to administration of a seasonal vaccine proved to be safe and tolerable among the elderly subjects.

Conclusion: the prime-boost approach demonstrates the cross strain immunity induced by the M-001 administration of HAI that is the regulatory criteria for efficacy: Priming with M-001 induces cross strain immunity that result in elevated seroconversion to influenza strains within the TIV and also to other drifting strains as compared to their baseline and to the respective placebos that are representing the response to the TIV alone. The elevated HAI is shown by % of seroconverted participants, in 10 out of 13 viruses tested, an increase was found, in 9 of them, the priming with the M-001 have led to at least 30% seroconverted subjects which is the minimal percentage required by the regulatory authorities for approved vaccines in this age group. For 5 of the viruses, the control group that was vaccinated with adjuvanted PBS and with a whole dose of TIV did not reach this 30% limit whereas this limit was achieved in the primed group. The universality of the M-001 vaccine is demonstrated herein using the standard measure of HAI and showing increased immunity to the strains included in the vaccine and to drifting strains of H1N1, H3N2 and influenza B from both Victoria and Yamagata lineages.

Example 5

BVX-004-Phase IIa Human Study of M-001

Aim: to assess the safety and immunogenicity of the M-001 alone, together with a commercial trivalent (TIV) influenza vaccine, and as a primer for a subsequent partial dose of the TIV.

A total of 200 subjects, both male and female, 18-49 years old, were participated in the trial. The participants were divided into 6 groups receiving the following:
  I—two doses, 21 days apart, of 500 µg adjuvated M-001 and a partial (15%) dose of TIV 60 days after the second immunization;
  II—two doses, 21 days apart, of placebo and a partial (15%) dose of TIV 60 days after the second immunization;
  III—two doses, 21 days apart, of adjuvated placebo;
  IV—two doses, 21 days apart, of 500 µg adjuvated M-001 co-administered with a 15% dose of TIV;
  V—two doses, 21 days apart, of 500 µg adjuvated M-001 co-administered with a 50% dose of TIV;
  VI—two doses, 21 days apart, of placebo and a 50% dose of TIV 60 days after the second immunization;

Antibody and cellular responses were measured in all patients including: levels of IgG antibodies, neutralization of complement, HAI responses against various strains of influenza, as well as proliferation of Interleukin 2 (IL-2) and interferon-gamma (IFN-γ)

Figure 11A:
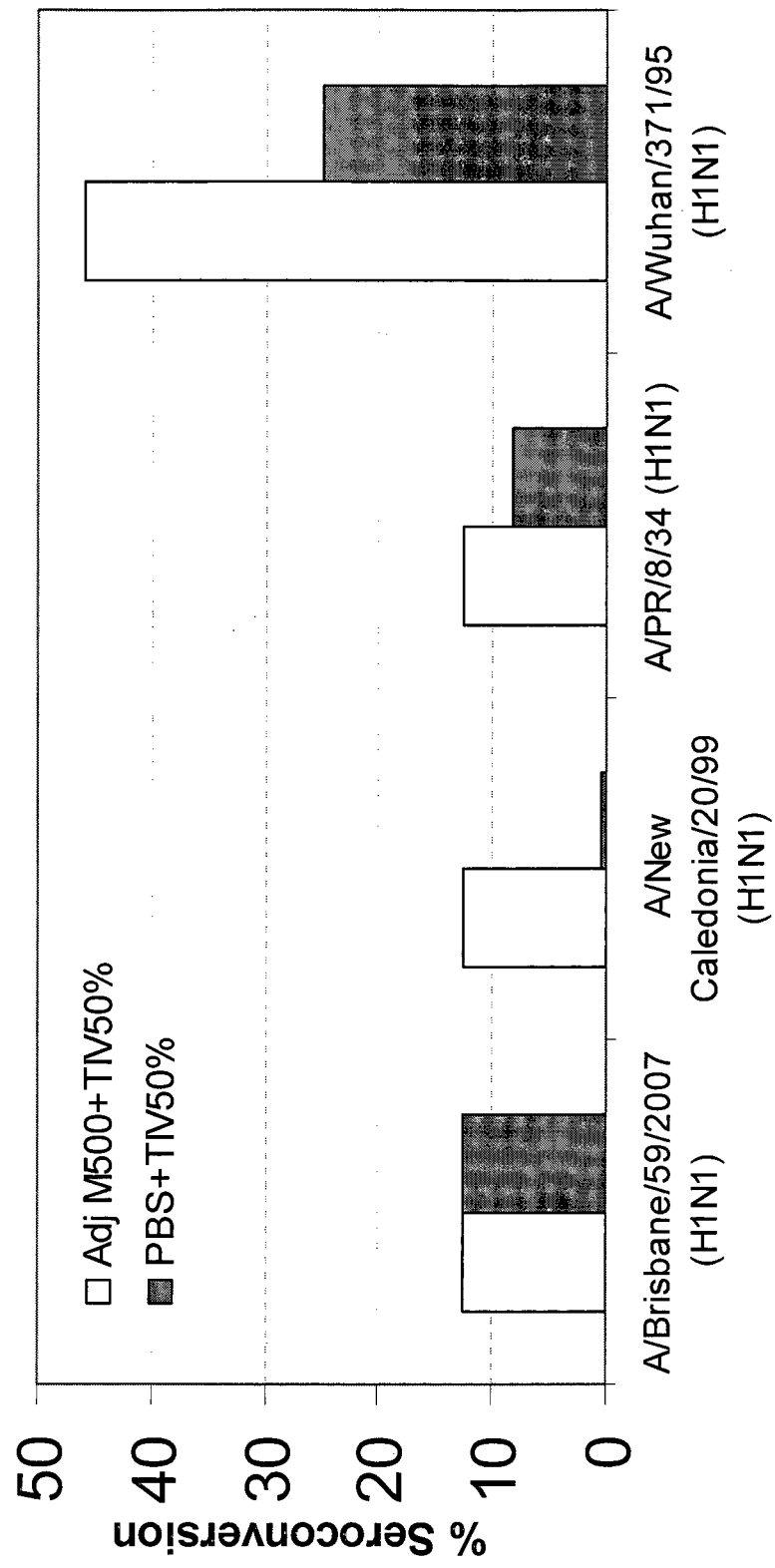
Figure 11B:
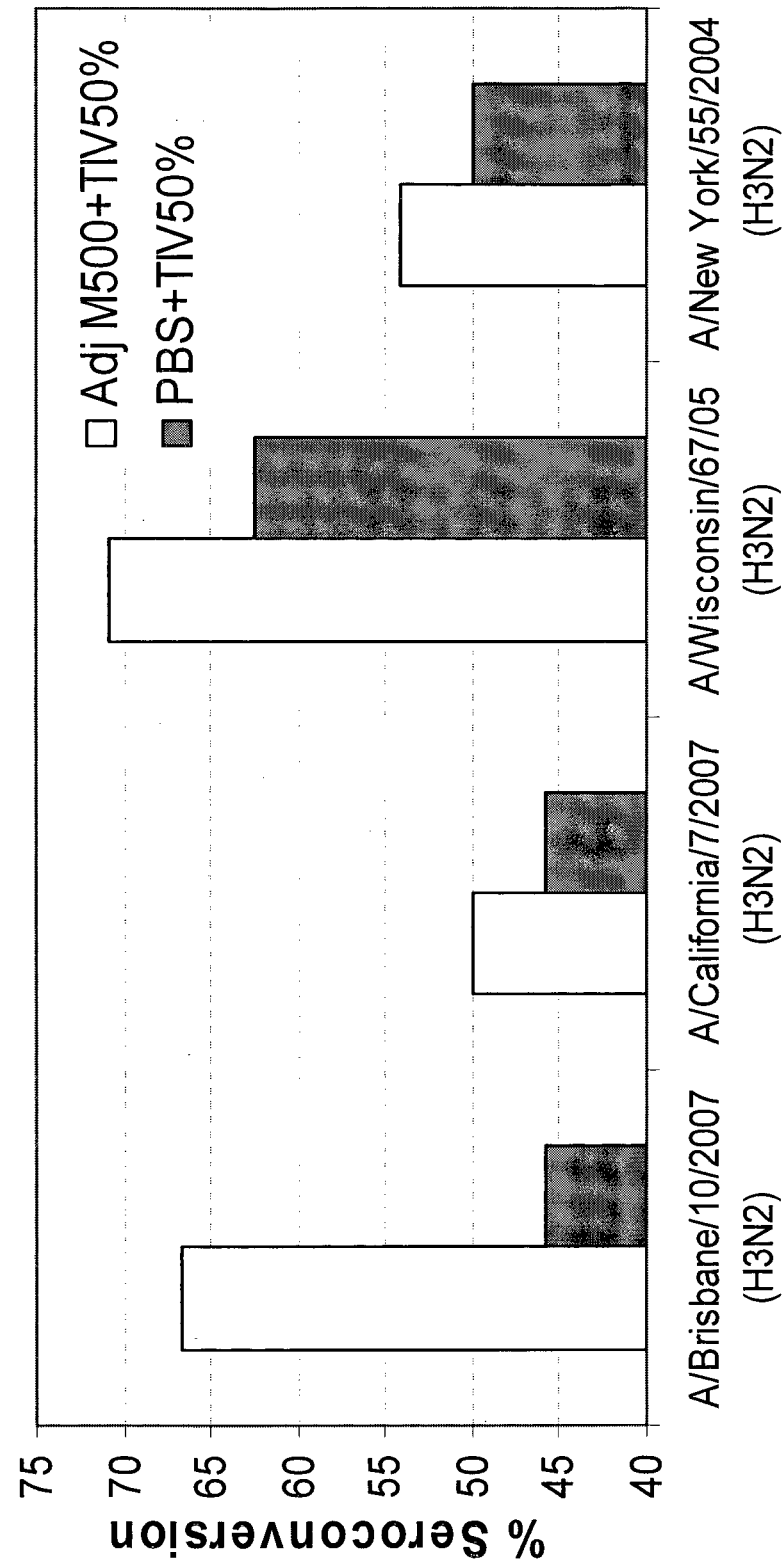
Figure 11C:
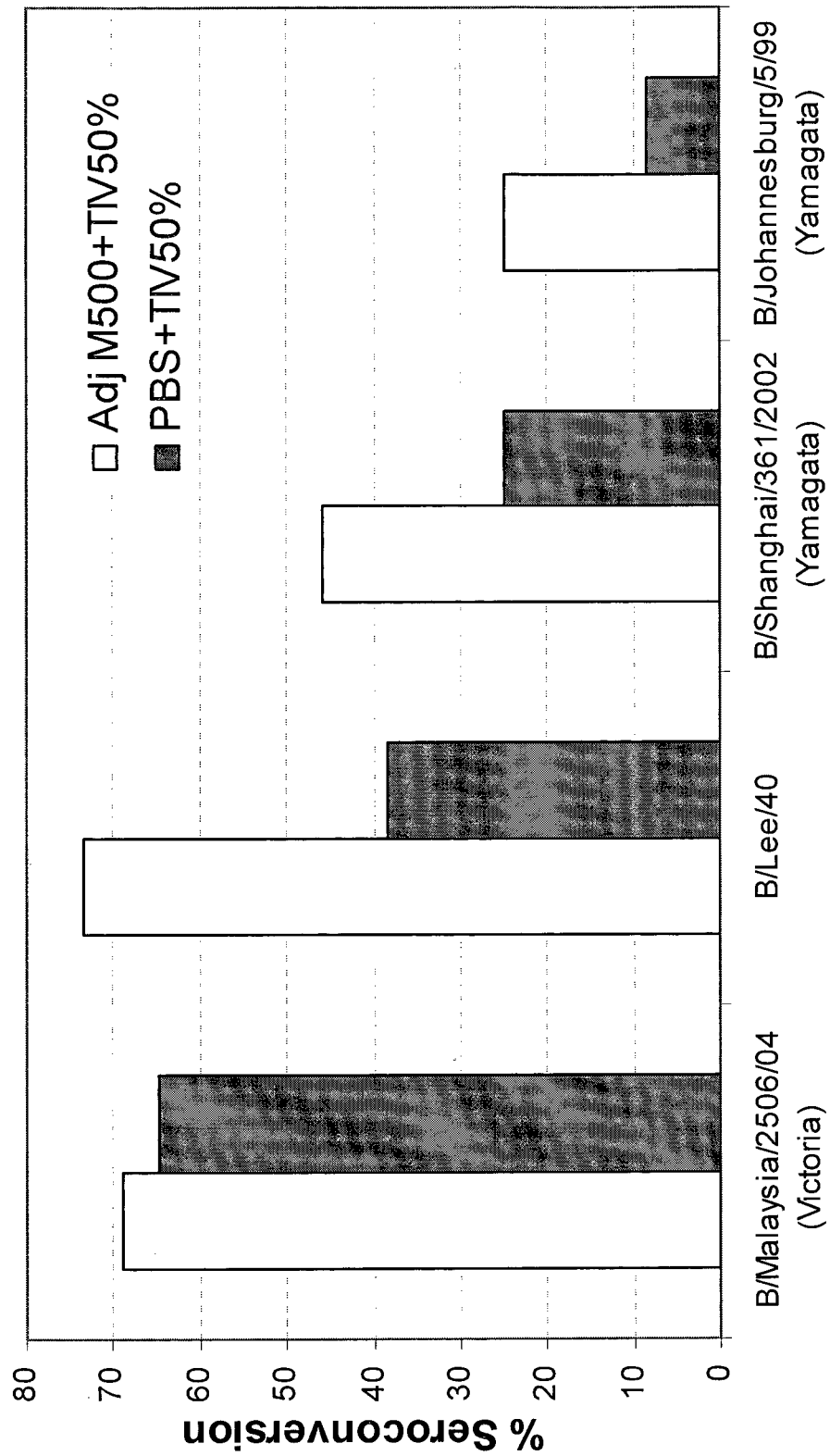

Interim HAI results following a single co-administration of Adjuvanted M-001 (500 mcg) with 50% of the conventional seasonal vaccine dose (TIV), vs. the control group consisting of participants immunized once with 50% TIV only, indicated that in 11 of 12 virus strains (H1N1, H3N2 and influenza B) not included in the seasonal vaccine administered, an increase in HAI response was demonstrated (FIGS. 11A-11C). In 6 of 12 virus strains, an enhancement of at least 10% in seroconversion proportion or at least 25% improvement of GMT was demonstrated. FIGS. 11A-C show results of co-administration of seasonal lowered dose (50% of standard dose) of TIV with adjuvanted M-001 polypeptide improved heterologous HAI titres recognizing virus strains not included in the seasonal TIV administered. HAI titres recognizing A/H1N1 (A), A/H3N2 (B) and influenza B (C) virus strains that were not included in the seasonal TIV administered were improved in subjects co-administered with both seasonal TIV plus adjuvanted M-001 for several different strains tested. Percent of seroconverted subjects was calculated as a) the number of subjects per cohort expressing a mean fold increase in anti-HA antibody levels ≥4-fold compared to levels in sera collected on day 0, with b) HAI titers ≥40 post-immunization.

These preliminary results demonstrate that co-administration of M-001 with a 50% dose of a conventional seasonal vaccine enhances HAI seroconversion and broaden the cross immunity against influenza strains.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A method for improving a protective effect or enhancing the efficacy of seasonal or pandemic influenza vaccine comprising administering to a subject an effective amount of a synthetic or recombinant multimeric polypeptide comprising multiple copies of a plurality of influenza virus peptide epitopes, wherein the multimeric polypeptide has three repetitions of nine conserved linear epitopes arranged in the following block copolymer structure [E1E1E1-E2E2E2-E3E3E3-E4E4E4-E5E5E5-E6E6E6-E7E7E7-E8E8E8-E9E9E9], wherein E1 is HA 354-372 (SEQ ID NO: 82), E2 is HA 91-108 (SEQ ID NO: 48), E3 is M1 2-12 (SEQ ID NO: 25), E4 is HA 150-159 (SEQ ID NO: 52), E5 is HA 143-149 (SEQ ID NO: 51), E6 is NP 206-229 (SEQ ID NO: 64), E7 is HA 307-319 (SEQ ID NO: 59 or 89), E8 is NP 335-350 (SEQ ID NO: 69), and E9 is NP 380-393 (SEQ ID NO: 70), and wherein the multimeric polypeptide is administered 1-5 weeks prior to administration of a seasonal or pandemic vaccine.

2. The method according to claim 1, wherein the multimeric polypeptide is administered 10-25 days prior to administration of a seasonal or pandemic influenza vaccine.

3. The method according to claim 1, wherein the amount of seasonal or pandemic influenza vaccine administered is 15-50% of a standard dose of said vaccine.

4. The method according to claim 1, wherein improvement in a protective effect is for influenza strains included in a seasonal or pandemic vaccine.

5. The method according to claim 1, wherein improvement in a protective effect is for influenza strains not included in a seasonal or pandemic vaccine.

6. The method according to claim 1, wherein improvement in a protective effect is measured as sero-protection in Hemagglutination Inhibition (HAI) response.

7. The method according to claim 1, wherein the subject is equal to or older than 55 years of age.

8. The method according to claim 1, wherein the polypeptide further comprises a carrier sequence.

9. The method according to claim 1, wherein the pandemic vaccine is against human, swine or avian influenza strains.

* * * * *

UNITED STATES PATENT AND TRADEMARK OFFICE
CERTIFICATE OF CORRECTION

PATENT NO. : 9,303,070 B2  
APPLICATION NO. : 14/000815  
DATED : April 5, 2016  
INVENTOR(S) : Ben-Yedidia et al.

It is certified that error appears in the above-identified patent and that said Letters Patent is hereby corrected as shown below:

IN THE SPECIFICATION

Column 1:
Line 4, after the title of the application and before the first heading, insert
-- This application is a 371 filing of International Patent Application PCT/IL2011/000178 filed February 22, 2011. --

Signed and Sealed this
Thirty-first Day of May, 2016

Michelle K. Lee
*Director of the United States Patent and Trademark Office*